United States Patent
Liu et al.

(10) Patent No.: US 7,282,126 B2
(45) Date of Patent: Oct. 16, 2007

(54) SYSTEM AND METHOD FOR DETERMINING KNOWN DNA VARIANTS WITH TEMPERATURE GRADIENT ELECTROPHORESIS

(75) Inventors: Zhaowei Liu, Port Matilda, PA (US); Zhiyong Guo, State College, PA (US); Christina Maye, State College, PA (US); Kevin R. Gutshall, State College, PA (US)

(73) Assignee: SpectruMedix LLC, State College, PA (US)

( * ) Notice: Subject to any disclaimer, the term of this patent is extended or adjusted under 35 U.S.C. 154(b) by 668 days.

(21) Appl. No.: 10/617,750

(22) Filed: Jul. 14, 2003

(65) Prior Publication Data

US 2004/0076947 A1 Apr. 22, 2004

Related U.S. Application Data

(63) Continuation of application No. 10/287,826, filed as application No. PCT/US01/27440 on Sep. 4, 2001, now Pat. No. 7,175,750.

(60) Provisional application No. 60/386,006, filed on Jul. 16, 2002, provisional application No. 60/395,614, filed on Jul. 15, 2002, provisional application No. 60/229,302, filed on Sep. 1, 2000.

(51) Int. Cl.
*G01N 27/453* (2006.01)

(52) U.S. Cl. .................. 204/450; 204/456; 204/452

(58) Field of Classification Search ............... 204/450, 204/451, 452, 461, 456, 616, 621, 608, 457
See application file for complete search history.

(56) References Cited

U.S. PATENT DOCUMENTS 5,066,377 A 11/1991 Rosenbaum et al.

(Continued)

FOREIGN PATENT DOCUMENTS

EP 0 329 341 A2 8/1989

(Continued)

OTHER PUBLICATIONS

Abrams et al., "Comprehensive Detection of Single Base Changes in Human Genomic DNA Using Denaturing Gradient Gel Electrophoresis and a GC Clamp," Genomics, vol. 7, pp. 463-475 (1990).

(Continued)

*Primary Examiner*—Alex Noguerola
(74) *Attorney, Agent, or Firm*—McQuaide, Blasko, Fleming & Faulkner, Inc.

(57) ABSTRACT

The present invention relates to a method of determining the genotype of a sample polynucleotide having at least a first variant site. At least a portion of the sample polynucleotide is amplified to obtain first amplicons, the first amplicons including the first variant site. The first amplicons are combined with first and second different polynucleotide controls, the first and second polynucleotide controls differing by at least one base therealong, the position of the at least one differing base corresponding to the first variant site of the sample polynucleotide. A plurality of first duplexes are prepared, each of at least some of the first duplexes comprising (i) a polynucleotide strand of one of the first amplicons and (ii) a complementary polynucleotide strand of the first polynucleotide control. A plurality of second duplexes are prepared, each of at least some of the second duplexes comprising (i) a polynucleotide strand of one of the first amplicons and (ii) a complementary polynucleotide strand of the second polynucleotide control. The first and second duplexes are subjected to temperature gradient electrophoresis (TGE) to obtain first and second electrophoresis data. The genotype of the first variant site of the sample polynucleotide is determiend based on the first and second electrophoresis data.

14 Claims, 20 Drawing Sheets

Formation of homo- and heteroduplexes

U.S. PATENT DOCUMENTS

| | | | |
|---|---|---|---|
| 5,068,176 A | 11/1991 | Vijg et al. ..................... 435/6 | |
| 5,734,058 A | 3/1998 | Lee | |
| 5,736,025 A | 4/1998 | Smith et al. | |
| 5,795,720 A | 8/1998 | Henco et al. .................. 435/6 | |
| 5,871,908 A | 2/1999 | Henco et al. .................. 435/6 | |
| 5,935,522 A | 8/1999 | Swerdlow et al. ............ 422/70 | |
| 5,998,147 A | 12/1999 | Petit et al. | |
| 6,017,704 A | 1/2000 | Herman et al. | |
| 6,036,831 A | 3/2000 | Bishop ...................... 204/618 | |
| 6,265,171 B1 | 7/2001 | Herman et al. | |
| 6,265,557 B1 | 7/2001 | Diamond et al. | |
| 6,398,933 B1 | 6/2002 | Scott ......................... 204/466 | |
| 6,475,721 B2 | 11/2002 | Kleiber et al. | |
| 6,486,309 B1 | 11/2002 | Gerber et al. | |
| 6,613,508 B1 | 9/2003 | Ness et al. | |
| 2002/0012902 A1 | 1/2002 | Fuchs et al. | |
| 2002/0042060 A1 | 4/2002 | Raees et al. .................. 435/6 | |

FOREIGN PATENT DOCUMENTS

| | | |
|---|---|---|
| WO | WO91/02815 | 3/1991 |
| WO | WO96/08715 | 3/1996 |
| WO | WO96/24687 | 8/1996 |
| WO | WO 96/24687 | 8/1996 |
| WO | WO 97/40184 | 10/1997 |
| WO | WO97/40184 | 10/1997 |
| WO | WO 01/77386 | 10/2001 |
| WO | WO 02/31199 | 4/2002 |

OTHER PUBLICATIONS

Alper, Joseph, "Biotechnology: Weighing DNA for Fast Genetic Diagnosis," Science Magazine, vol. 279:5359, pp. 2044-2045 (1998).

Chee et al., "Accessing Genetic Information with High-Density DNA Arrays," Science Magazine, vol. 274, No. 5287, Oct. 1996, pp. 610-614 (pp. 1-13).

Gelfi et al., "Detection of point mutations by capillary electrophoresis in liquid polymers in temporal thermal gradients," Electrophoresis, 1994, vol. 15, pp. 1506-1511.

Henco et al., "Quantitative PCR: the determination of template copy numbers by temperature gradient gel electrophoresis (TGGE)," Nucleic Acids Research, vol. 18, No. 22, pp. 6733-6734.

Igloi, Gabor L., "Automated Detection of Point Mutations by Electrophoresis in Peptide-Nucleic Acid-Containing Gels", BioTechniques, 27:798-808 (1999).

Ke et al., "Selecting DNA fragments for mutation detection by temperature gradient gel electrophoresis: Application to the p53 gene cDNA," Electrophoresis, 1993, vol. 14, pp. 561-565.

Khrapko et al., "Constant denaturant capillary electrophoresis (CDCE): a high resolution approach to mutational analysis," Nucleic Acids Research, 1994, vol. 22, No. 3, pp. 364-369.

Myers et al., "Detection of single base substitutions in total genomic DNA," Nature, Feb. 1985, vol. 313, pp. 495-498.

Ray et al., "Peptide nucleic acid (PNA): its medical and biotechnical applications and promise for the future", Department of Physical Chemistry, Chalmers University of Technology, S 412 96, Gothenburg, Sweden, pp. 1041-1060.

Riesner et al., "Temperature-gradient gel electrophoresis of nucleic acids: Analysis of conformational transitions, sequence variations, and protein-nucleic acid interactions," Electrophoresis, 1989, vol. 10, pp. 377-389.

Riesner et al., "Temperature-gradient gel electrophoresis for the detection of polymorphic DNA and for quantitative polymerase chain reaction," Electrophoresis, 1992, vol. 13, pp. 632-636.

Sidransky, David, "Nucleic Acid-Based Methods for the Detection of Cancer," Science, vol. 278, Nov. 7, 1997, www.sciencemag.org, pp. 1054-1058.

Taylor et al., "Detection of Mutations and Polymorphisms on the WAVE™ DNA Fragment Analysis System," Transgenomic, Application Note 101.

Wang, David G., "Large-Scale Inditification, Mapping, and Genotyping of Single-Nucleotide Polymorphisms in the Human Genome," Science, vol. 280, May 15, 1998, pp. 1077-1082.

Wartell et al., "Detecting single base substitutions, mismatches and bulges in DNA by temperature gradient gel electrophoresis and related methods", Journal of Chromatography, pp. 169-185 (1998).

Wiese et al., "Scanning for mutations in the human prion protein open reading frame by temporal terperature gradient gel electrophoresis", Electrophoresis, pp. 1851-1860 (1995).

"High-Throughput Detection of Unknown Mutations By Using Multiplexed Capillary Eletrophoresis With Polyvinylpyrrolidone Solution", The Ames Laboratory, U.S. Department of Energy by Iowa State University, pp. 1-28.

Qiufeng Gao et al., 25. High-Speed High-Throughput Mutation Detection, http://www.ornl.gov/sci/techresources/Human_Genome/publicat/00santa/25.html, Research Abstracts, 2000, DOE Human Genome Program.

entries for "Peltier Effect", "thermoelectric heating", "thermoelectric cooling" and "thermoelectric cooler" in the McGraw-Hill Encyclopedia of Science & Technology Online. Downloaded on Jun. 6, 2005.

International Preliminary Examination Report from PCT/US01/27440, mailed Jan. 9, 2003.

Gao et al., "High-Throughput Detectin of Unknown Mutations by Using Multiplexed Capillary Electrophoresis With Poly(vinylpyrrolidone) Solution," Jun. 1, 2000, *Analytical Chemistry*, vol. 72, No. 11, pp. 2499-2506.

Schell et al., "Detection of point mutations by capillary electrophoresis with temporal temperature gradients," 1999, *Electrophoresis*, vol. 20, pp. 2864-2869.

Henco et al., "Quantitative PCR: the determination of template copy numbers by temperature gradient gel electrophoresis (TGGE)," Nucleic Acids Research, vol. 18, No. 22, pp. 6733-6734, 1990.

Khrapko et al, "Constant denaturant capillary electrophoresis (CDCE): a high resolution approach to mutational analysis," Nucleic Acids Research, 1994, vol. 22, No. 3, pp. 364-369.

Ray et al., "Peptide nucleic acid (PNA): its medical and biotechnical applications and promise for the future", Department of Physical Chemistry, Chalmers University of Technology, S 412 96, Gothenburg, Sweden, pp. 1041-1060, Jun. 2000.

Riesner et al., "Temperature-gradient gel electrophoresis of nucleic acids: Analysis of conformational transitions, sequence variations, and protein-nucleic acid interactions," Electrophoresis, 1989, vol. 10, pp. 377-389.

Riesner et al., "Temperature-gradient gel electrophoresis for the detection of polymorphic DNA and for quantitative polymerase chain reaction," Electrophoresis, 1992, vol. 13, pp. 632-636.

Taylor et al., "Detection of Mutations and Polymorphisms on the WAVE™ DNA Fragment Analysis System," Transgenomic, Application Note 101, publication date is unknown.

"High-Throughput Detection of Unknown Mutations By Using Multiplexed Capillary Electrophoresis With Polyvinylpyrrolidone Solution" The Ames Laboratory, U.S. Department of Energy by Iowa State University, pp. 1-28, Mar. 2, 2000.

Qiufeng Gao et al., 25. High-Speed High-Throughput Mutation Detection, http://www.ornl.gov/sci/techresources/Human_Genome/publicat/00santa/25.html, Research Abstracts, 2000, DOE Human Genome Program.

entries for "Peltier Effect", "thermoelectric heating", "thermoelectric cooling" and "thermoelectric cooler" in the McGraw-Hill Encyclopedia of Science & Technology Online. Downloaded on Jun. 6, 2005.

Individual Peak Magnification

Individual Peak Magnification

FIG. 15

| Cap # | Sample ID | Control # | Control Type | Mutation Score | Call | Confidence Score | Comments |
|---|---|---|---|---|---|---|---|
| D01 [ 37 ] | | D07 [ 43 ] | CC | 227 | + | 100 | |
| D02 [ 38 ] | | D07 [ 43 ] | CC | 191 | + | 100 | |
| D03 [ 39 ] | | D07 [ 43 ] | CC | 110 | + | 100 | |
| D04 [ 40 ] | | D07 [ 43 ] | CC | 6 | - | 0 | |
| D05 [ 41 ] | | D07 [ 43 ] | CC | 274 | + | 100 | |
| D06 [ 42 ] | | D07 [ 43 ] | CC | 7 | - | 0 | |
| D07 [ 43 ] | | D07 [ 43 ] | CC | 0 | - | 0 | |
| D08 [ 44 ] | | D07 [ 43 ] | CC | 183 | + | 100 | |
| D09 [ 45 ] | | D09 [ 45 ] | TT | 0 | - | 0 | |
| E01 [ 49 ] | | D09 [ 45 ] | TT | 28 | + | 20 | |
| E02 [ 50 ] | | D09 [ 45 ] | TT | 171 | + | 100 | |
| E03 [ 51 ] | | D09 [ 45 ] | TT | 122 | + | 100 | |
| E04 [ 52 ] | | D09 [ 45 ] | TT | 186 | + | 100 | |
| E05 [ 53 ] | | D09 [ 45 ] | TT | 9 | - | 0 | |
| E06 [ 54 ] | | D09 [ 45 ] | TT | 158 | + | 100 | |

GenoType Call Result

| No. | Sample ID | Cap Number | GenoType | Comments |
|---|---|---|---|---|
| 1 | . | 37:49 | TT | |
| 2 | . | 38:50 | CT | |
| 3 | . | 39:51 | CT | |
| 4 | . | 40:52 | CC | |
| 5 | . | 41:53 | TT | |
| 6 | . | 42:54 | CC | |

FIG. 16

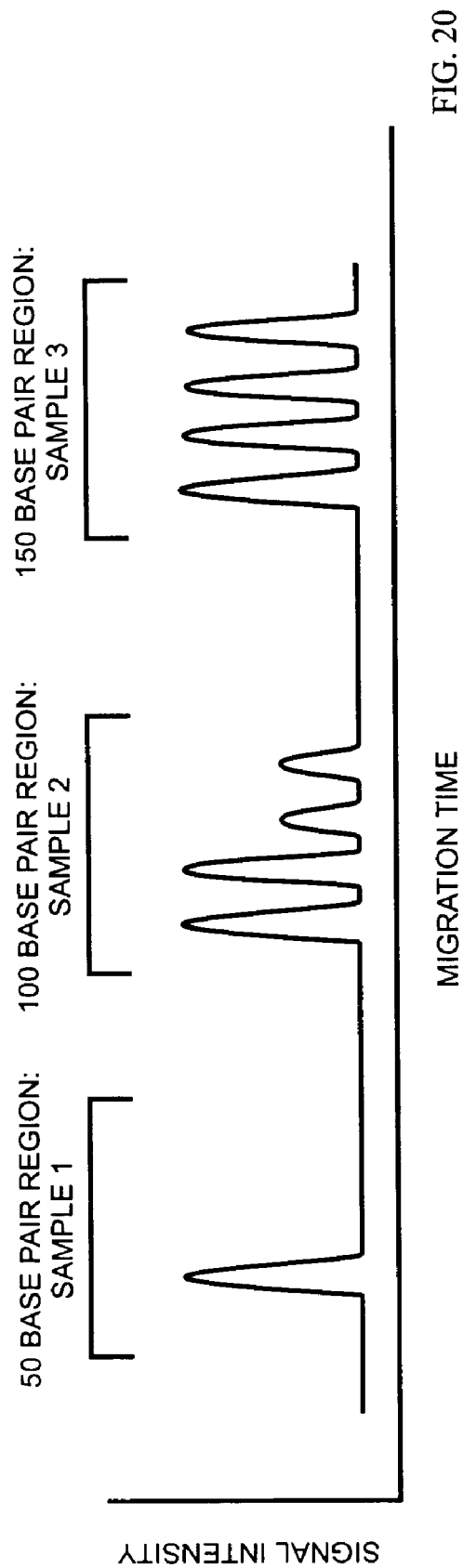
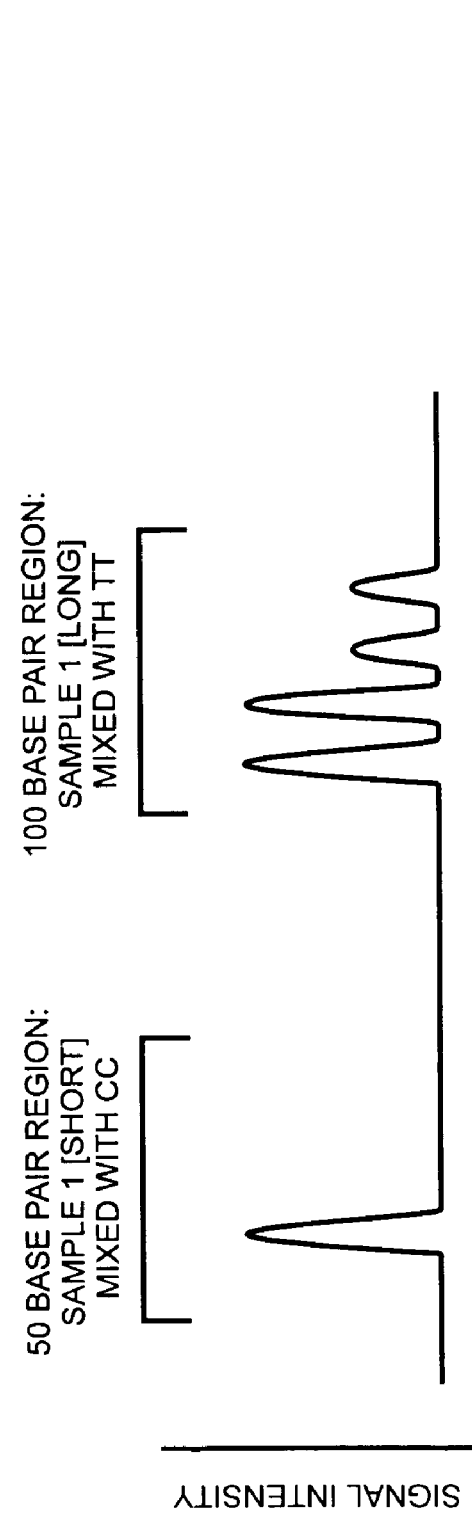
FIG. 20
FIG. 21

SYSTEM AND METHOD FOR DETERMINING KNOWN DNA VARIANTS WITH TEMPERATURE GRADIENT ELECTROPHORESIS

RELATED APPLICATIONS

The present application claims priority to U.S. Provisional Application Nos. 60/395,614, filed Jul. 15, 2002 and 60/386,006, filed Jul. 16, 2002. The present application is also a continuation of U.S. application Ser. No. 10/287,826, filed Nov. 5, 2002, now U.S. Pat. No. 7,175,750 which claims priority to international application no. PCT/US01/274401, filed Sep. 4, 2001, which claims priority to U.S. Provisional Application No. 60/229,302, filed Sep. 1, 2000. Each of the foregoing applications is incorporated by reference in its entirety.

FIELD OF THE INVENTION

The present invention relates to a system and method for determining variants in polynucleotides, such as DNA and in particular genomic DNA.

BACKGROUND OF THE INVENTION

Efficient, fast and cost-effective techniques are still required for analyses of single nucleotide polymorphisms (SNPs) and known mutations associated with disease. Many methods have been developed for SNP/mutation genotyping (Landergren et al. 1998). The DNA-chip method based on hybridization may allow processing large numbers of samples, but it requires careful calibration of the signal when interpreting data (Wang et al. 1998). Single base extension (SBE) followed by separation with capillary electrophoresis using automated sequencing instrument is limited by the length of the extension primer that can be synthesized by present technology. For instance, no more than 10 SBE products are separated in a single capillary using the Applied Biosystems' SNaPshot kit (from Protocol of ABI Prism SNaPshot Multiplex Kit, 2000). Detection of SBE reactions by mass spectrometry requires highly purified products, which can be costly and labor-intensive (Ross et al. 1998). For a more thorough review of the field, please see a number of papers published in a supplement to BioTechniques, June 2002, under the title—SNPs: Discovery of markers for disease.

SUMMARY OF THE INVENTION

A first aspect of the invention relates to a method of determining the genotype of a sample polynucleotide having at least a first variant site. The method may comprise amplifying at least a portion of the sample polynucleotide to obtain first amplicons, the first amplicons including the first variant site. The position of the first variant site along the sample nucleotide is preferably known. The first amplicons may be combined with first and second different polynucleotide controls. The first and second polynucleotide controls may differ by at least one base therealong, the position of the at least one differing base preferably corresponds to the position of the first variant site along the sample polynucleotide.

A plurality of first duplexes may be prepared. At least some and preferably each of at least some of the first duplexes may comprise (i) a polynucleotide strand of one of the first amplicons and (ii) a complementary polynucleotide strand of the first polynucleotide control. A plurality of second duplexes may be prepared. At least some and preferably each of at least some of the second duplexes comprising (i) a polynucleotide strand of one of the first amplicons and (ii) a complementary polynucleotide strand of the second polynucleotide control.;

The first and second duplexes may be subjected to temperature gradient electrophoresis (TGE) to obtain first and second electrophoresis data, which are indicative of the genotype of the first variant site. The genotype of the first variant site of the sample polynucleotide may be determined based on the first and second electrophoresis data. The determination of the genotype may comprise determining a number of peaks present in the first electrophoresis data and a number of peaks present in the second electrophoresis data.

The first duplexes and second duplexes may be subjected to TGE along first and second different separation lanes, such as along the bores of different capillaries.

The first and second polynucleotide controls may be wild-type polynucleotides.

The method may comprise amplifying at least a second different portion of the sample polynucleotide to obtain second amplicons, the second amplicons including a second variant site of the sample polynucleotide. The position of the second variant site along the sample polynucleotide is preferably known. The second amplicons may be combined with third and fourth different polynucleotide controls, the third and fourth polynucleotide controls differing by at least one base therealong. The position of the at least one differing base may correspond to the second variant site of the sample polynucleotide.

A plurality of third duplexes may be prepared. Each of at least some of the third duplexes may comprise (i) a polynucleotide strand of one of the second amplicons and (ii) a complementary polynucleotide strand of the third polynucleotide control. A plurality of fourth duplexes may be prepared. Each of at least some of the fourth duplexes may comprise (i) a polynucleotide strand of one of the second amplicons and (ii) a complementary polynucleotide strand of the fourth polynucleotide control.

The third and fourth duplexes may be subjected to temperature gradient electrophoresis (TGE) to obtain third and fourth electrophoresis data, which are indicative of the genotype of the second variant site of the first sample polynucleotide. The genotype of the second variant site of the sample polynucleotide may be determined based on the third and fourth electrophoresis data.

At least one and preferably both of the first and second duplexes may have a size that differs from at least one and preferably both of the third and fourth duplexes. Subjecting the first and second duplexes to TGE and subjecting the third and fourth duplexes to TGE comprise simultaneously subjecting at least 3 and preferably 4 duplexes of the first, second, third, and fourth duplexes to TGE along the same separation lane. At least one and preferably both of the first and second duplexes may have a size that differs from at least one of the third and fourth duplexes by at least 20 base pairs.

The method may comprise amplifying at least a first portion of a second different sample polynucleotide to obtain second amplicons. The second sample polynucleotide comprises a second variant site. The position of the second variant site along the second sample polynucleotide may be known. The second amplicons may include the second variant site of the sample polynucleotide. The second amplicons and third and fourth different polynucleotide controls may be combined. The third and fourth polynucleotide controls may differ by at least one base therealong. The position of the at least one differing base may correspond to the second variant site of the second sample polynucleotide.

A plurality of third duplexes may be prepared. Each of at least some of the third duplexes may comprise (i) a polynucleotide strand of one of the second amplicons and (ii) a complementary polynucleotide strand of the third polynucleotide control. A plurality of fourth duplexes may be prepared. Each of at least some of the fourth duplexes may comprise (i) a polynucleotide strand of one of the second amplicons and (ii) a complementary polynucleotide strand of the fourth polynucleotide control. The third and fourth duplexes may be subjected to temperature gradient electrophoresis (TGE) to obtain third and fourth electrophoresis data, which are indicative of the genotype of the second variant site of the sample polynucleotide. The genotype of the second variant site of the second sample polynucleotide may be determined based on the third and fourth electrophoresis data.

At least one or both of the first and second duplexes may have a size that differs from at least one or both of the third and fourth duplexes. Subjecting the first and second duplexes to TGE and subjecting the third and fourth duplexes to TGE may comprise simultaneously subjecting at least 3 and preferably 4 duplexes of the first, second, third, and fourth duplexes to TGE along the same separation lane. At least one of the first and second duplexes has a size that differs from at least one of the third and fourth duplexes by at least 20 base pairs.

Another embodiment of the invention relates to a method for determining the genotype of a sample polynucleotide. The method may comprise providing first and second polynucleotide controls. The first and second polynucleotide controls may differ by at least one base therealong. The position of the differing base may correspond to a position of a variant site of the sample polynucleotide. The position of the variant site along the sample polynucleotide is preferably known.

A first amount of the sample polynucleotide may be combined with the first polynucleotide control to prepare a first mixture. Each of the sample polynucleotide and the first polynucleotide control may comprise a polynucleotide strand sufficiently complementary to form a duplex with a polynucleotide strand of the other of the sample polynucleotide and first polynucleotide control.

First duplexes may be prepared. At least some of the first duplexes may comprise a strand of the sample polynucleotide and a strand of the first polynucleotide control A first amount of the sample polynucleotide with the second polynucleotide control to prepare a second mixture. Each of the sample polynucleotide and the second polynucleotide control may comprise a polynucleotide strand sufficiently complementary to form a duplex with a polynucleotide strand of the other of the sample polynucleotide and second polynucleotide control.

Second duplexes may be prepared. At least some of the second duplexes may comprise a strand of the sample polynucleotide and a strand of the second polynucleotide control.

The first and second mixtures may be subjected to temperature gradient electrophoresis to obtain first and second electrophoresis data, which is indicative of the genotype of the variant site of the sample polynucleotide. The genotype of the sample polynucleotide may be determined based on the first and second electrophoresis data.

Determining the genotype of the sample polynucleotide may comprise determining a number of peaks present in the first electrophoresis data and a number of peaks present in the second electrophoresis data. One or both the first and second polynucleotide controls may be homozygous.

The sample polynucleotide may comprise one or more amplicons prepared by amplifying at least one and preferably two first double stranded polynucleotides. Each of the at least at least one first double stranded polynucleotides may comprise genomic DNA of an organism such as mammal (e.g., a human) or a plant.

Another embodiment of the invention relates to a method for determining the genotype of a first variant site of a first sample polynucleotide. The method may comprise providing amplicons of the of the first sample polynucleotide, the amplicons including the first variant site. A first portion of the amplicons may be subjected to denaturing and annealing to prepare a first mixture.

A first polynucleotide control may be provided. The first polynucleotide control may comprise at least one polynucleotide strand able to form a duplex with a polynucleotide strand of at least one of the amplicons. The first polynucleotide control may have a base corresponding to the first variant site of the sample polynucleotide, the identity of the base may be known. The position of the variant site along the first sample polynucleotide may be known.

A second mixture may be prepared by combining a second portion of the amplicons with the first polynucleotide control. The second mixture may be subjected to denaturing and annealing to prepare a third mixture.

The first mixture may be subjected to temperature gradient electrophoresis (TGE) to obtain first electrophoresis data, which is indicative of the genotype of the first variant site. The second mixture to temperature gradient electrophoresis (TGE) to obtain second electrophoresis data, which is indicative of the genotype of the first variant site. The method may comprise determining the genotype of the first variant site of the sample polynucleotide based on the first and second electrophoresis data.

The step of subjecting a first portion of the amplicons to denaturing and annealing to prepare a first mixture may be performed prior to introducing the amplicons to an electrophoresis separation lane, such as prior to injecting the first portion of amplicons into a capillary. The step of subjecting the second mixture to denaturing and annealing to prepare a third mixture may be performed prior to introducing the second mixture to an electrophoresis separation lane, such as prior to injecting the second portion of amplicons into a capillary.

In one embodiment, the sample polynucleotide comprises a second variant site. The position of the second variant site along the sample polynucleotide may be known. Second amplicons of the of the first sample polynucleotide may be provided. The second amplicons may include the second variant site. A first portion of the second amplicons may be subjected to denaturing and annealing to prepare a fourth mixture.

A second polynucleotide control may be provided. The second polynucleotide control may comprise at least one polynucleotide strand able to form a duplex with a polynucleotide strand of at least one of the second amplicons. The second polynucleotide control may have a base corresponding to the second variant site of the first sample polynucleotide. The identity of the base may be known.

A second portion of the second amplicons may be combined with the second polynucleotide control to prepare a fifth mixture. The fifth mixture may be subjected to denaturing and annealing to prepare a sixth mixture.

The fourth mixture may be subjected to temperature gradient electrophoresis (TGE) to obtain third electrophoresis data, which is indicative of the genotype of the second variant site.

The sixth mixture may be subjected to temperature gradient electrophoresis (TGE) to obtain fourth electrophoresis data, which is indicative of the genotype of the second variant site. The genotype of the first variant site of the sample polynucleotide may be determined based on the first and second electrophoresis data.

The step of subjecting a first portion of the amplicons to denaturing and annealing to prepare a first mixture may be performed prior to introducing the amplicons to an electrophoresis separation lane, such as prior to injecting the first portion of amplicons into a capillary. The step of subjecting the second mixture to denaturing and annealing to prepare a third mixture may be performed prior to introducing the second mixture to an electrophoresis separation lane, such as prior to injecting the second portion of amplicons into a capillary.

In one embodiment, the method comprises providing second amplicons of a second sample polynucleotide. The second amplicons may include a second variant site of the second sample polynucleotide. The position of the second variant site along the second sample polynucleotide may be known.

A first portion of the second amplicons may be subjected to denaturing and annealing to prepare a fourth mixture.

A second polynucleotide control may be provided. The second polynucleotide control may comprise at least one polynucleotide strand able to form a duplex with a polynucleotide strand of at least one of the second amplicons. The second polynucleotide control may have a base corresponding to the second variant site of the second sample polynucleotide. The identity of the base may be known.

A second portion of the second amplicons may be combined with the second polynucleotide control to prepare a fifth mixture. The fifth mixture may be subjected to denaturing and annealing to prepare a sixth mixture.

The fourth mixture may be subjected to temperature gradient electrophoresis (TGE) to obtain third electrophoresis data, indicative of the second variant site of the second sample polynucleotide.

The sixth mixture to temperature gradient electrophoresis (TGE) to obtain fourth electrophoresis data, which is indicative of the second variant site of the second sample polynucleotide. The genotype of the second variant site of the second sample polynucleotide based on the first and second electrophoresis data.

The step of subjecting a first portion of the amplicons to denaturing and annealing to prepare a first mixture may be performed prior to introducing the amplicons to an electrophoresis separation lane, such as prior to injecting the first portion of amplicons into a capillary. The step of subjecting the fifth mixture to denaturing and annealing to prepare a third mixture may be performed prior to introducing the second mixture to an electrophoresis separation lane, such as prior to injecting the second portion of amplicons into a capillary.

BRIEF DESCRIPTION OF THE DRAWINGS

The present invention is discussed herein in reference to the drawings in which:

FIG. 15 illustrates a user interface of the invention;

FIG. 16 illustrates use of two scores to make a genotype call for a sample polynucleotide;

FIG. 20 illustrates schematic electrophoresis data as may be obtained by subjecting each of three different samples to TGE along the same separation lane; and FIG. 21 illustrates schematic electrophoresis data as may be obtained by subjecting different sized amplicons of a common portion of a sample polynucleotide to TGE in the presence of different control polynucleotides along the same separation lane.

DETAILED DESCRIPTION OF THE INVENTION

The present invention provides a powerful tool for studies of disease associations using SNPs as the DNA markers. It may be used in pharmacgenomics to relate individual genotypes to drug usages. The invention may also be used for disease diagnostics. There is an increasing demand for the genotyping technology for more efficient detection of DNA variations. A technical system disclosed here is suitable to conduct high throughput analysis for known mutations and single nucleotide polymorphisms (SNPs). Unlike use of temperature gradient electrophoresis for discovering unknown mutations (e.g., Gao and Yueng, 1999), the method of the present invention may be used for genotyping of known DNA variants (such as SNPs or mutations) in a genome. Thus, the exact locations of SNPs/mutations are determined in the art. The method in accordance with Gao and Yueng requires a sequencing step to locate the exact position of the mutation. In one embodiment of the present invention, at least one and preferably two or more homozygous DNA controls are added testing material in order to score all three possible genotypes in a diploid organism. The testing material may be analyzed in multiplexed fashion to increase efficiency of the technique.

Figure 1:
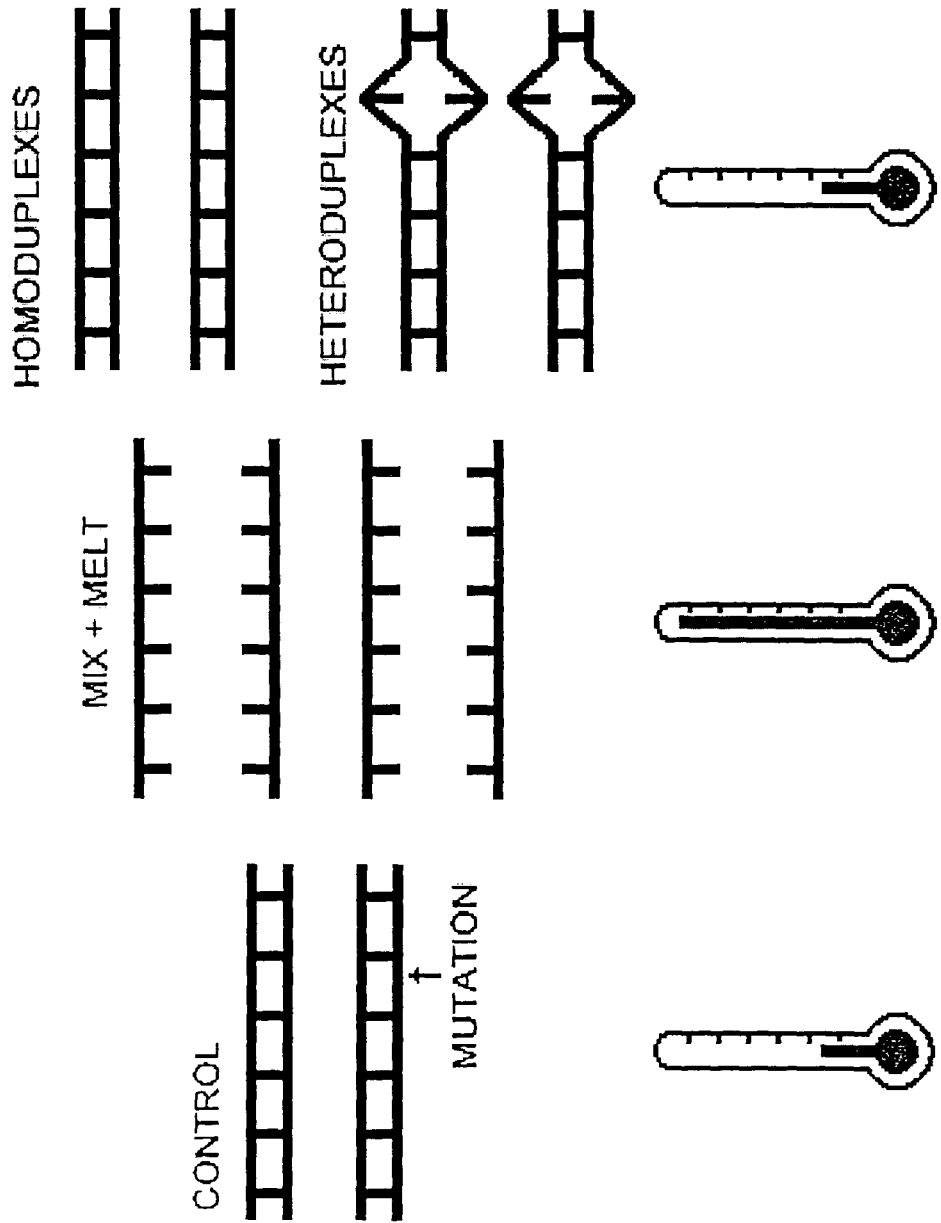
FIG. 1 illustrates preparation of homoduplexes and heteroduplexes.

Referring to FIG. 1, a TGE assay in accordance with the invention may be based on a heteroduplex analysis in which a heterozygous sample with a mutation/SNP is denatured and slowly annealed to form homoduplexes of original strands of polynucleotide and heteroduplexes each with a mismatch at the mutation/SNP site. In accordance with any embodiment of the invention, excess primers, if present, may be removed prior to the denaturing and annealing steps. These four species of DNA molecules have different melting temperatures (Tm), which are the temperatures at which half of the double-stranded DNA molecules dissociate (denature) and become single-stranded.

Figure 2:
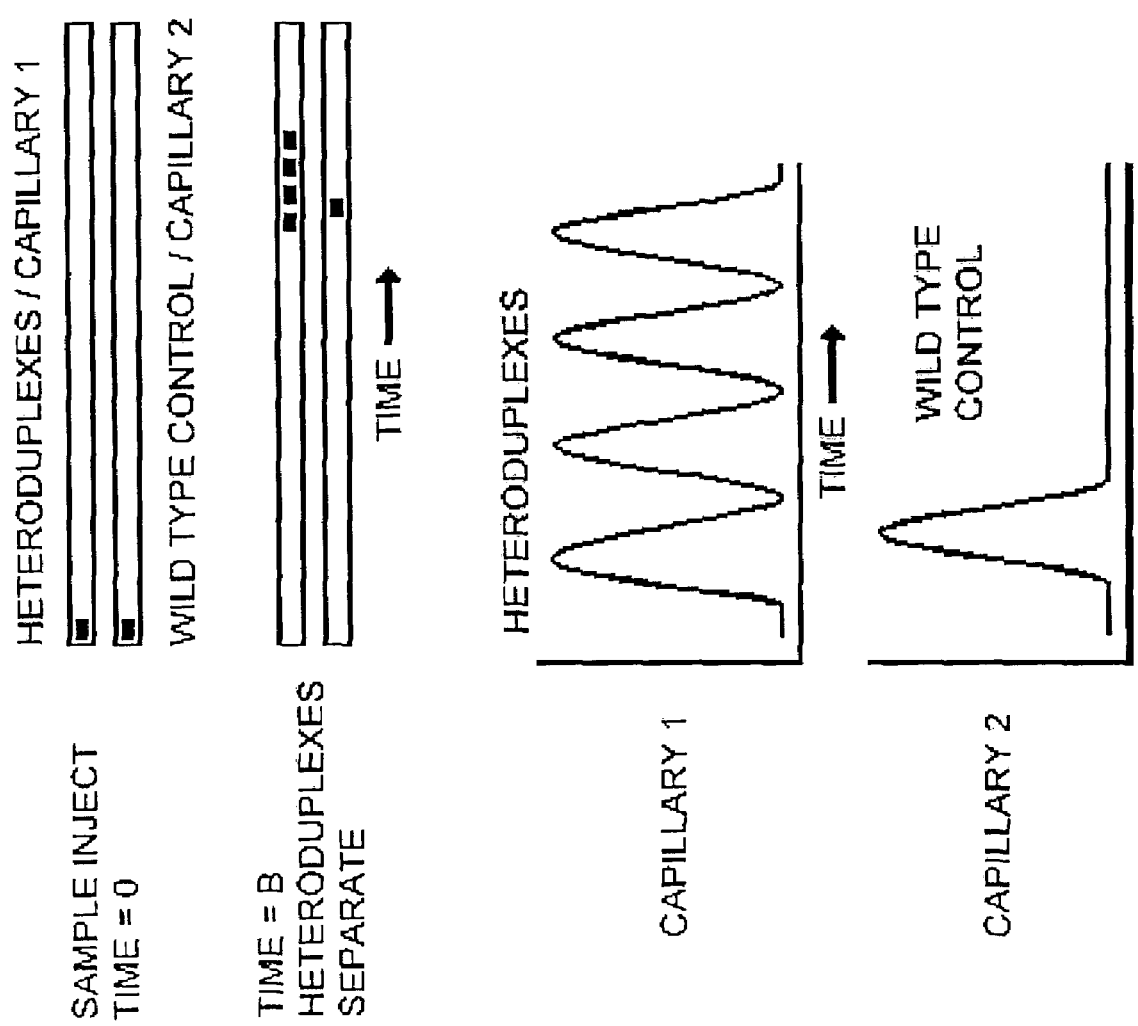
FIG. 2 illustrates temperature gradient electrophoresis separation of four species of homo- and heteroduplexes along a first separation lane in a sieving matrix and migration of a wild-type control along a second separation lane in a sieving matrix.

Referring to FIG. 2, a sample comprising duplexes is separated in a sieving medium preferably premixed with an intercalating dye. The migrating duplexes are subjected to a temperature gradient. Even though the homoduplexes having similar Tm's and the heteroduplexes have similar Tm's, the Tms for two heteroduplexes are usually lower. Thus, the Tms of two heteroduplexes will be reached first. When the Tm is reached, duplex will partially denature to form a bulky structure, which retards the migration of the duplex. The overall result is that the homoduplexes and heteroduplexes will separate from each other (FIG. 2). When, for example, they pass through the detection window, electrophoresis data may be obtained. The electrophoresis data is indicative of the separated duplexes. For example, when heteroduplexes are present, the electrophoresis data may contain more or broader peaks than will a wild-type control subjected to temperature gradient electrophoresis.

Depending on the steepness of the temperate gradient, a heterozygous sample can be resolved into four, three, two peaks or even a broad peak, compared to the control. The closer the ramping temperature to the Tm's of the sample, as well as the slower the rate of the ramp, the better the resolution can be achieved, i.e. more three-, four-peak patterns can be observed. However, if the purpose is to distinguish the mutation/SNP peak pattern from that of the control, one can use a broader ramp to scan various samples with different Tm's in a single test. The tested sample with a peak pattern distinguishable from the control will be sequenced in order to locate the exact position of the variant site. So, It may be unnecessary, in many cases, to resolve testing material into its highest resolution.

To score all three possible genotypes (i.e. CC, CT and TT) in a diploid organism, two TGE assays may be used to reveal these known sites of DNA variants. Each assay generates a genotype score for the testing sample. Scores obtained from two assays may be combined to produce a final call of genotype for the sample.

One embodiment of the invention comprises subjecting one or more sample polynucleotides (and/or one or more amplicons corresponding to at least a portion of the sample polynucleotides) to TGE in the absence of a control. Electrophoresis data is obtained from the TGE. The electrophoresis data may be used to determine a first score (shown schematically in the upper half of FIG. 3). The first score may be referred to as an initial determination of the genotype of each sample polynucleotide. Referring to FIG. 4, electrophoresis data and first scores for each of six sample polynucleotides are shown.

Figure 3:
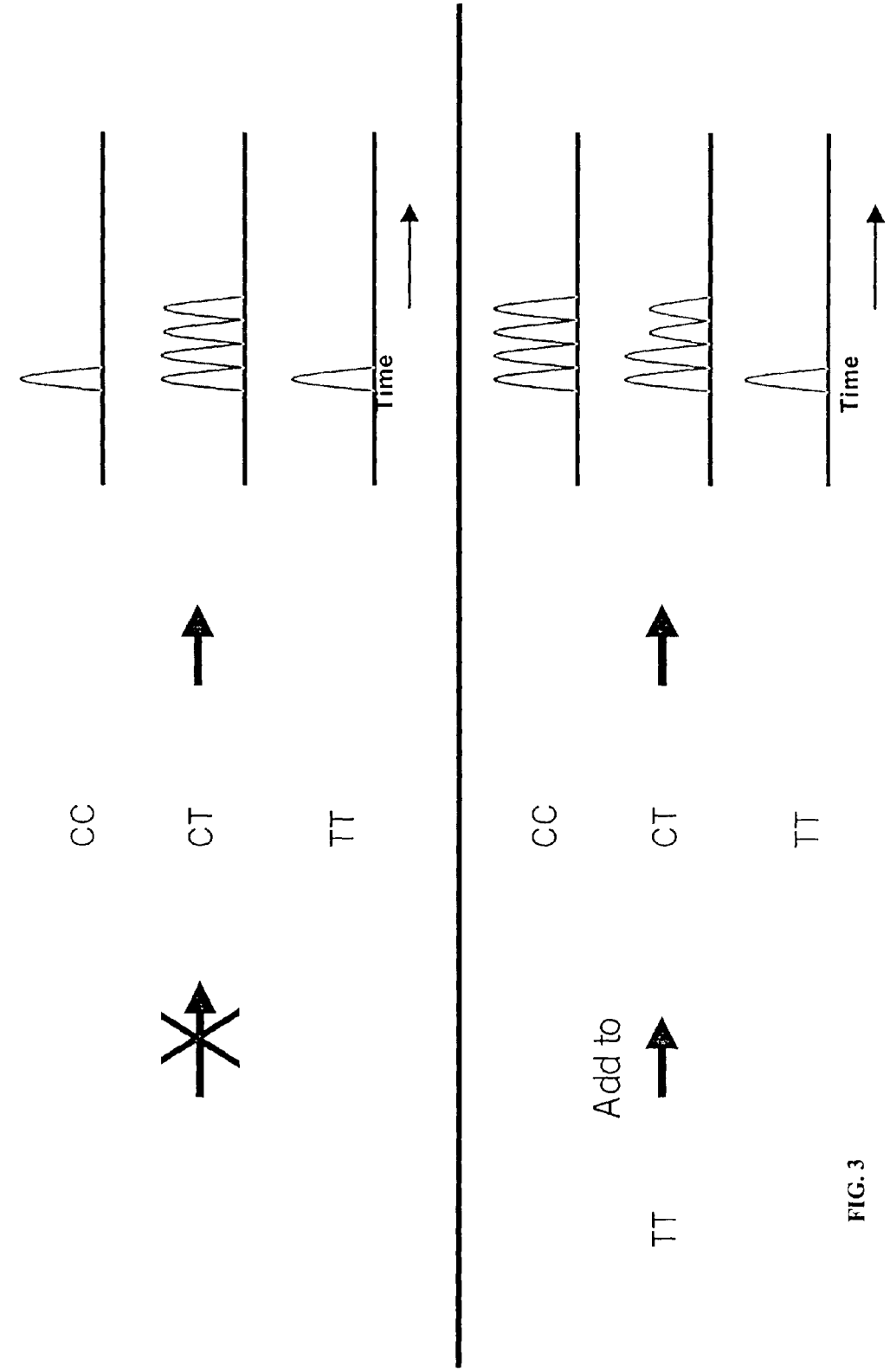
FIG. 3 illustrates schematic electrophoresis data as may be obtained for different genotypes in determination of DNA variants with TGE using a homozygous control.
Figure 4:
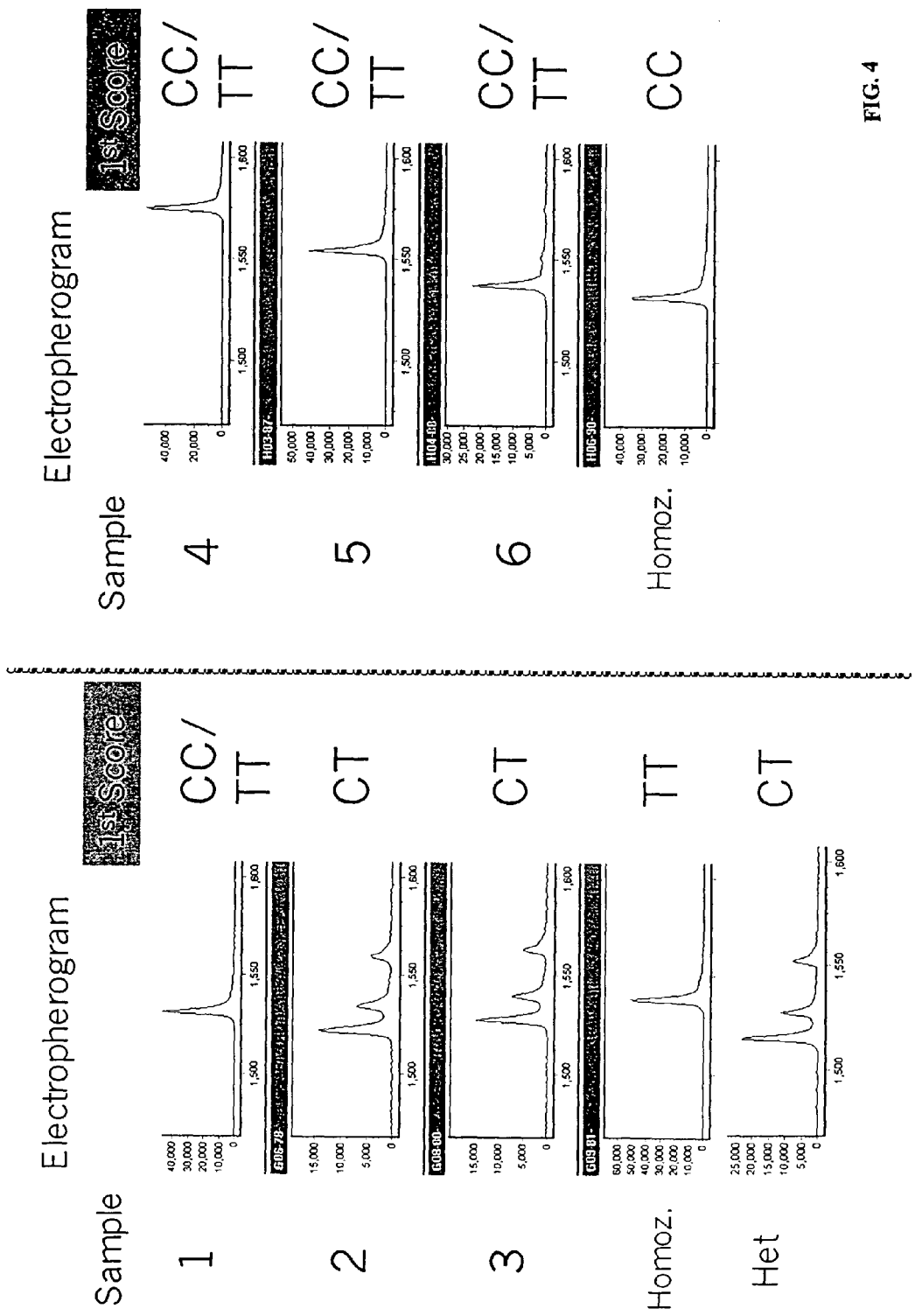
FIG. 4 shows electrophoresis data obtained in accordance with the scheme of FIG. 3: first genotype scores without addition of control to the sample polynucleotides, two homozygous controls (CC and TT), Het: one heterozygous control.

A second score may be obtained by subjecting the one or more sample polynucleotide (and/or one or more amplicons corresponding to at least a portion of the sample polynucleotides) to TGE in the presence of a control, which may be a homozygous or heterozygous control as shown schematically in the lower half of FIG. 3 showing use of a homozygous control. Electrophoresis data is obtained from the TGE separation. The control is preferably a duplex comprising first and second single stranded polynucleotides each preferably able to form a duplex with one or more strands of the one or more sample polynucleotides and or amplicons derived from the sample polynucleotides. For example, where the sample polynucleotide and or amplicons comprise two complementary polynucleotide strands, the control polynucleotide may comprise a first polynucleotide strand able to form a duplex with a first strand of the sample polynucleotide or amplicon and a second polynucleotide strand able to form a duplex with the complementary strand of the sample polynucleotide or amplicon.

Figure 5:
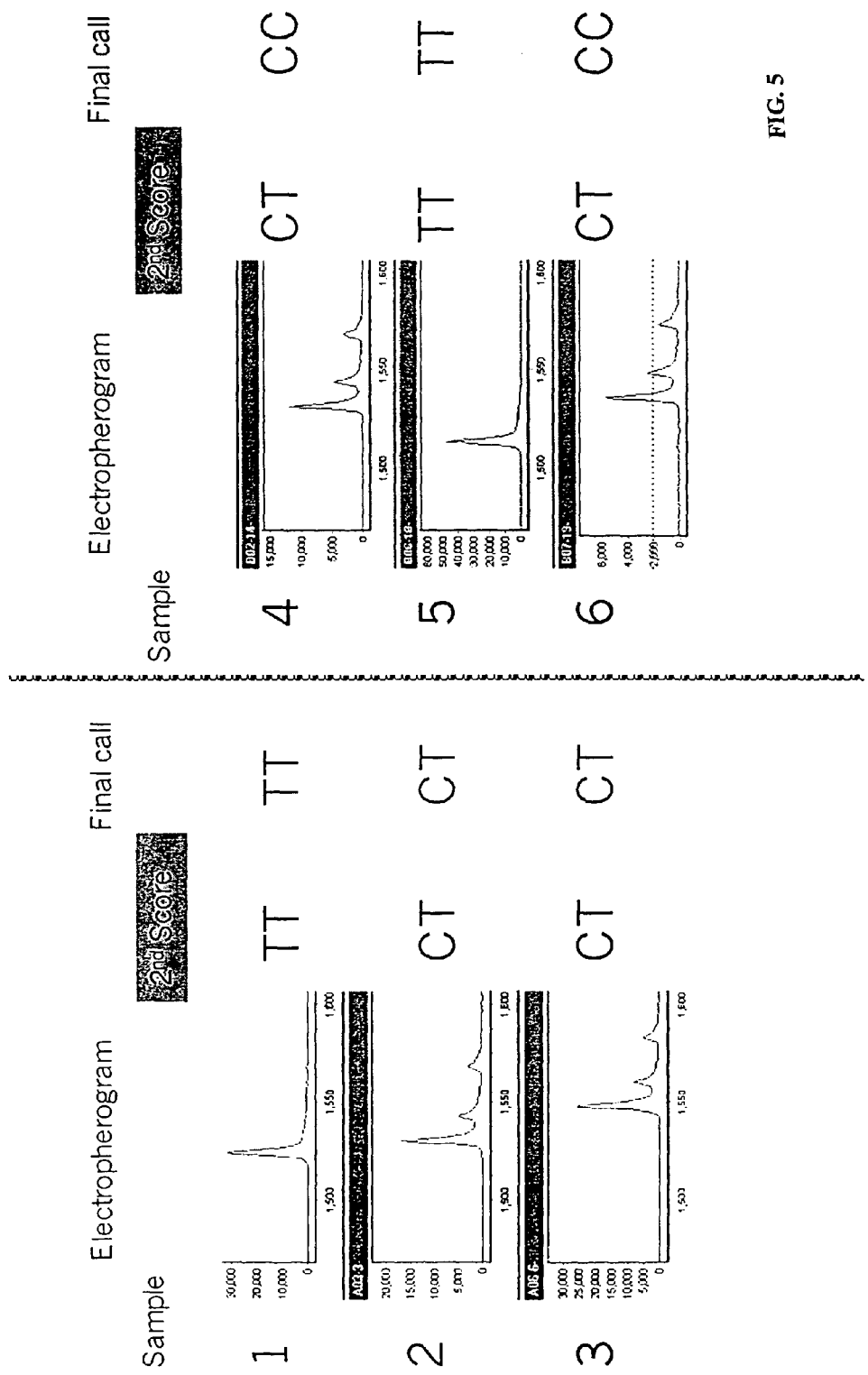
FIG. 5: shows experimental data obtained with in accordance with the scheme of FIG. 3, Second genotype scores with addition of a control polynucleotide to the sample polynucleotides.

The control and the one or more sample polynucleotides and or amplicons corresponding thereto are preferably subjected to at least one denaturing and annealing step prior to prepare duplexes. Referring to FIG. 5, electrophoresis data obtained from TGE of a TT control and of the sample polynucleotides of FIG. 4. The duplexes of the control and sample polynucleotides are prepared prior to obtaining the electrophoresis data and preferably prior to migrating the control and sample polynucleotides along an electrophoresis separation lane. Second scores obtained from the electrophoresis data FIG. 4 are also shown as are final scores indicative of the genotype of each of the six sample polynucleotides.

Figure 6:
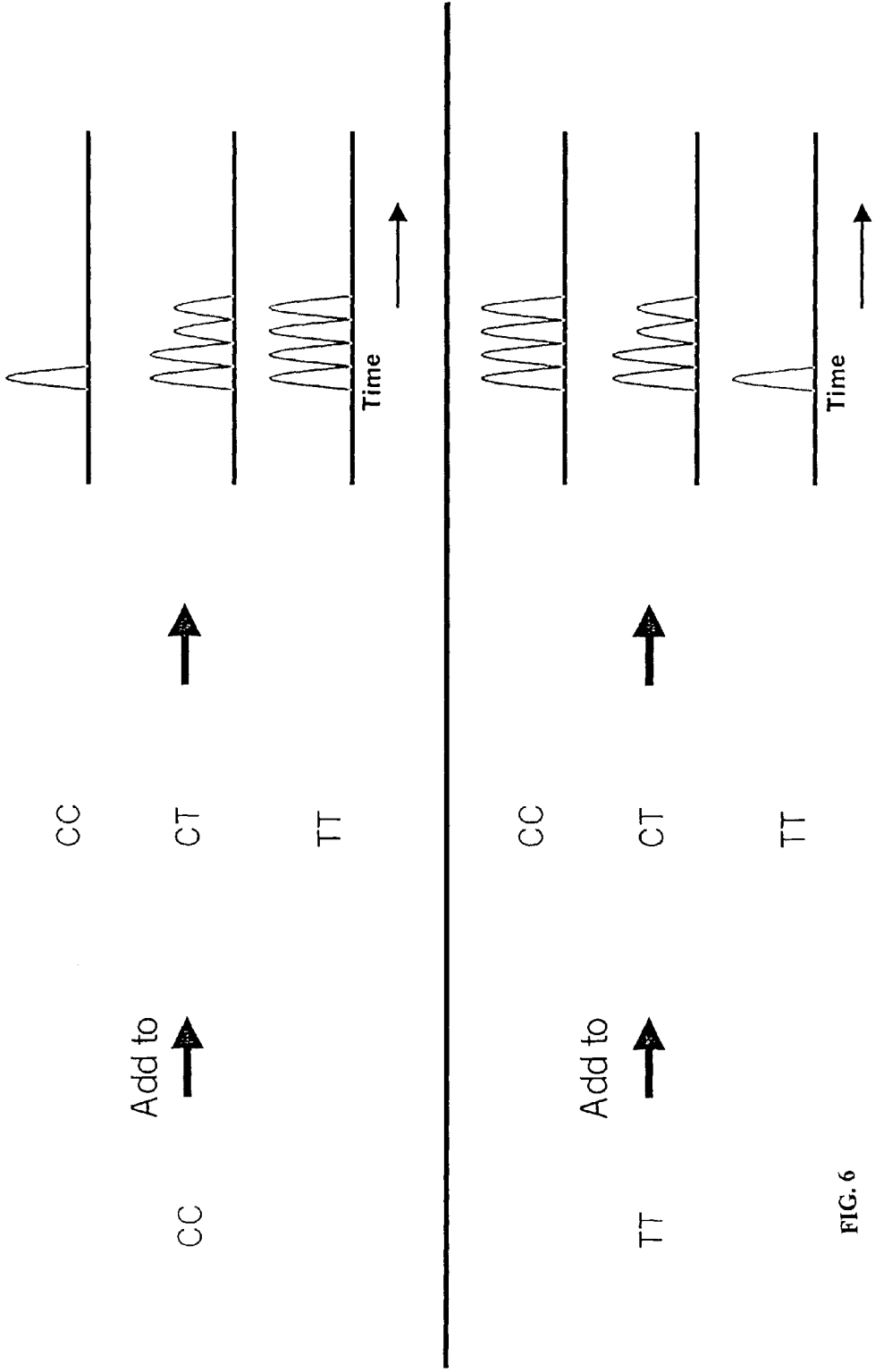
FIG. 6 illustrates schematic electrophoresis data as may be obtained for different genotypes in determining DNA variants with TGE using two homozygous controls.
Figure 7:
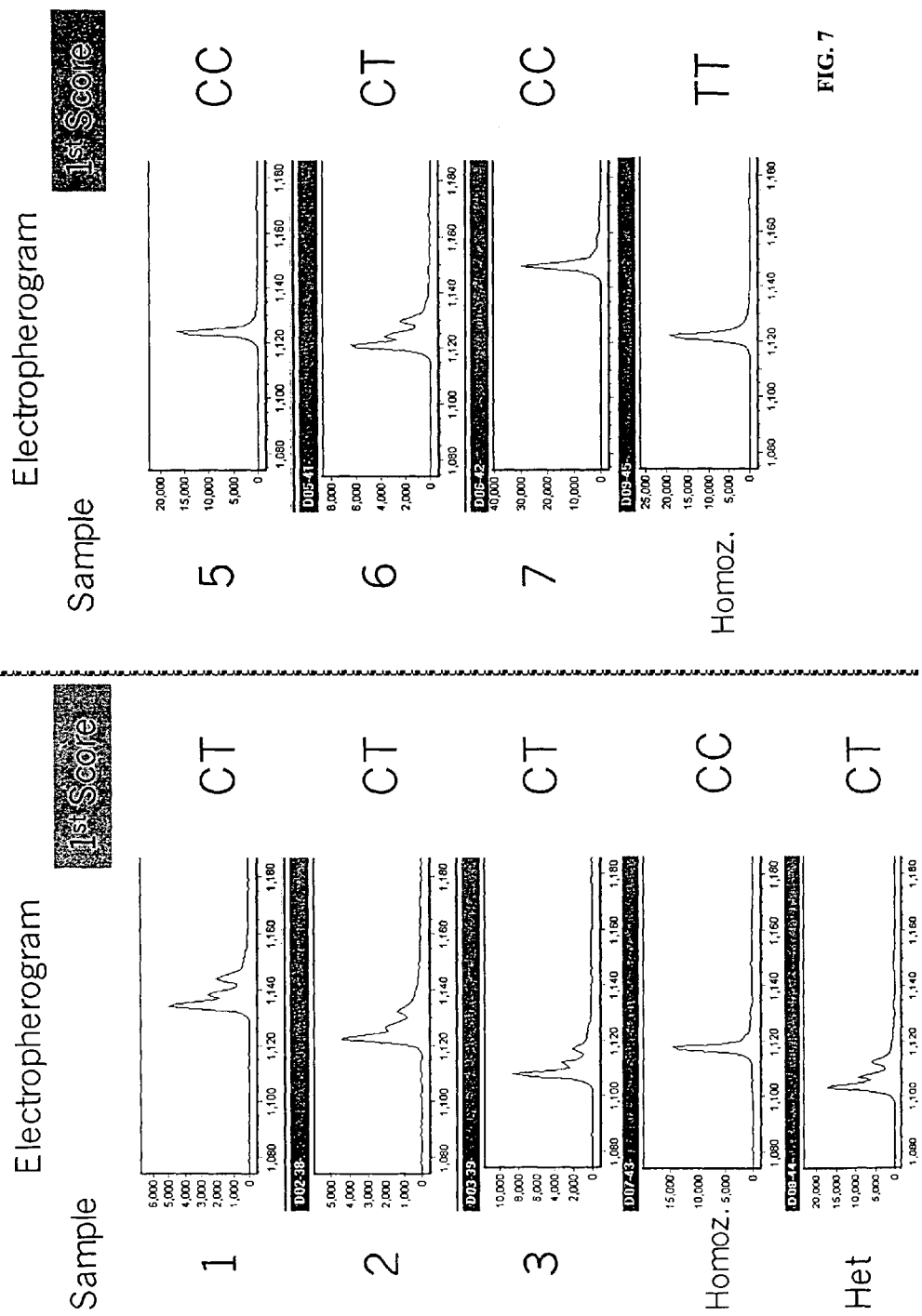
FIG. 7 shows electrophoresis data obtained in accordance with the scheme of FIG. 6: first genotype scores with addition of a first homozygous control to the samples.
Figure 8:
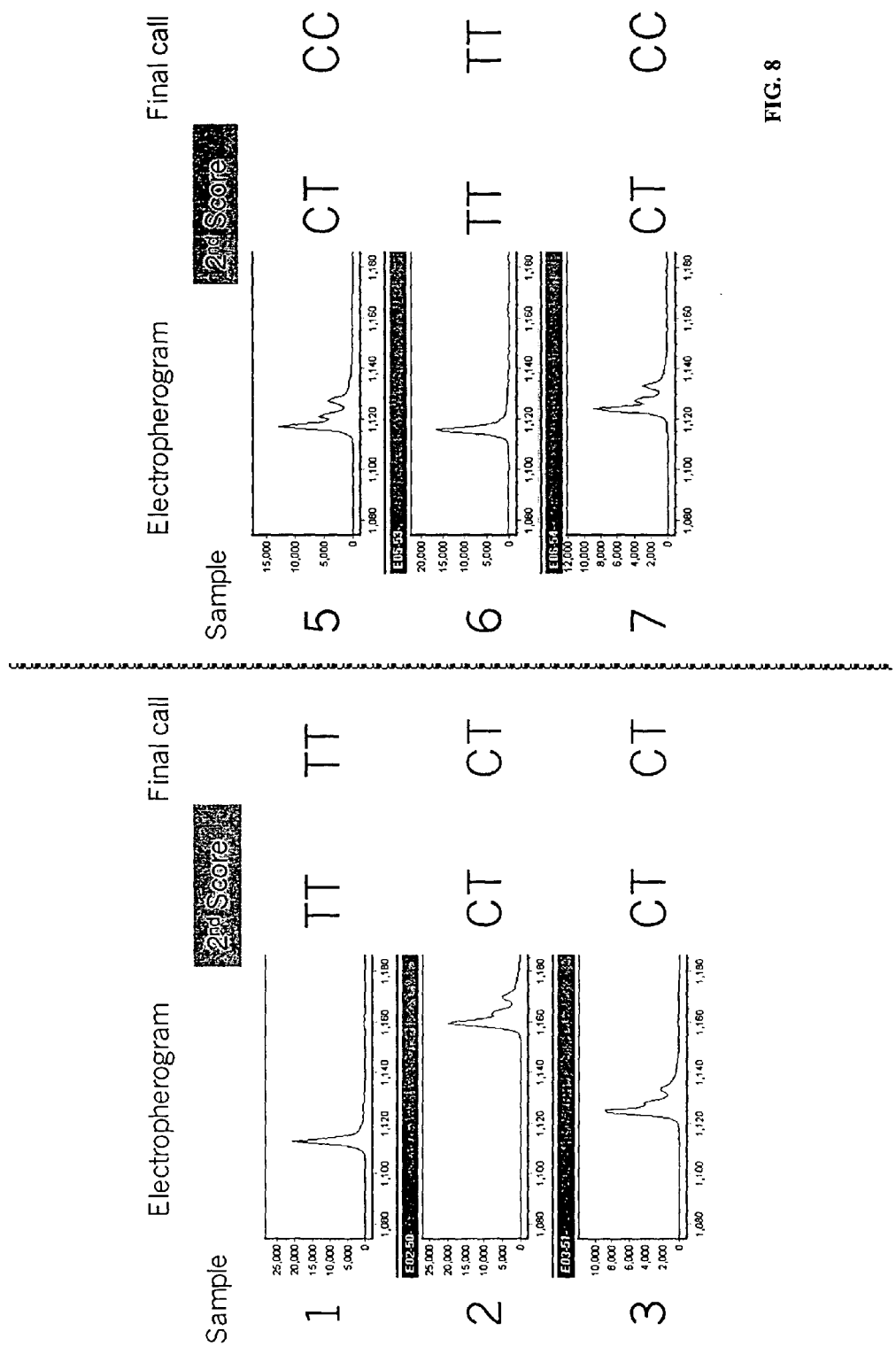
FIG. 8 shows electrophoresis data obtained in accordance with the scheme of FIG. 6: second genotype scores with addition of a second homozygous control to the samples.
Figure 9:
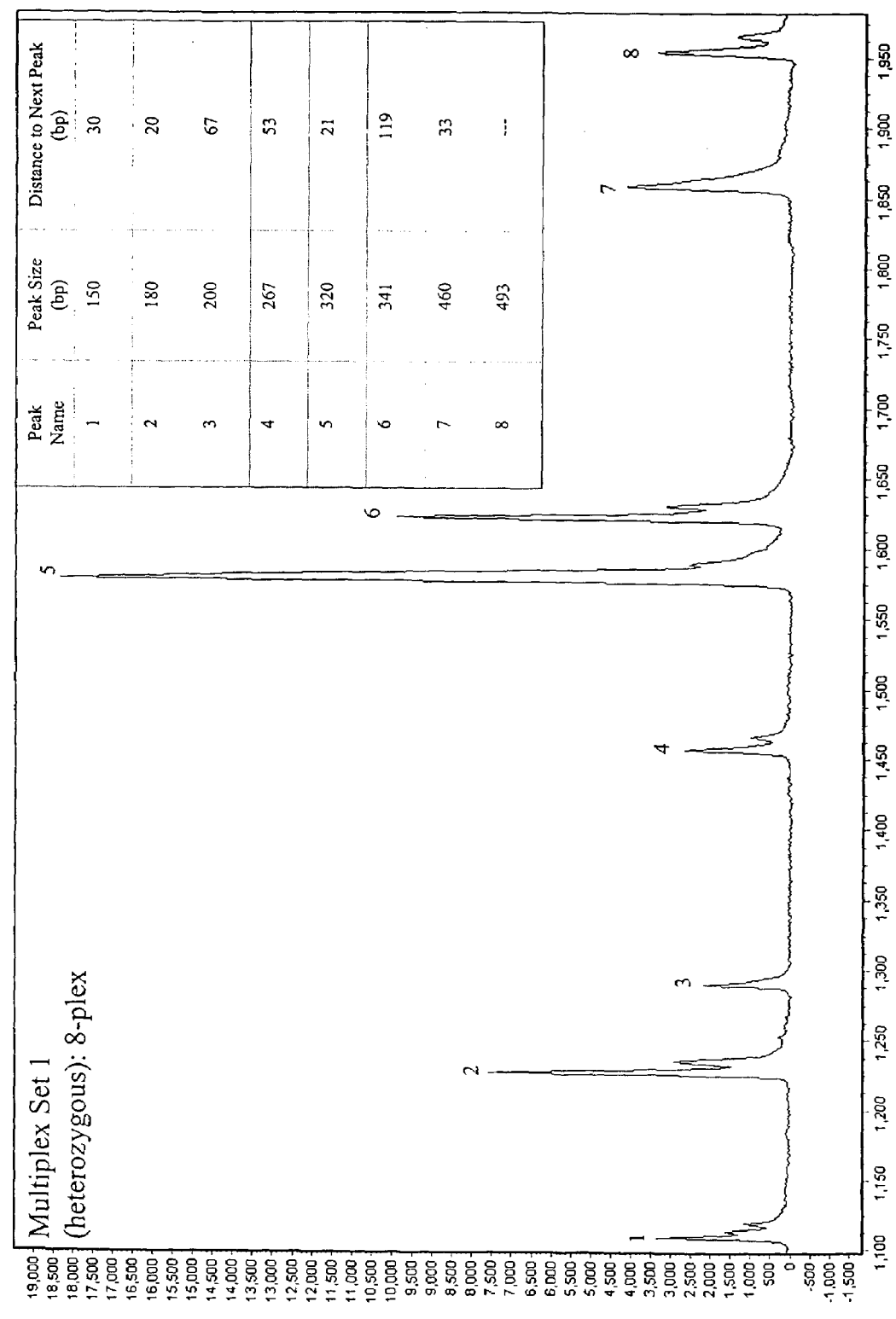
FIG. 9 shows electrophoresis data obtained from a multiplexed run of eight heterozygous samples along a single separation lane, X-axis: Frame number (migration time), Y-axis: electrophoresis data intensity, peak numbers, corresponding DNA sizes and size difference in base pairs to next peak, PEO sieving matrix.

Referring to FIG. 6, another embodiment of the invention comprises subjecting the sample polynucleotide (and/or one or more amplicons corresponding to at least a portion of the sample polynucleotides) to TGE in the presence of at least two controls, which may be, for example, homozygous or heterozygous. Electrophoresis data is obtained from the TGE separation. The electrophoresis data may be used to determine first and second scores for the sample polynucleotides or amplicons corresponding thereto. FIGS. 6, 7 and 8 schematically illustrates use of homozygous CC and TT controls.

Although homozygous controls are preferred, heterozygous controls may be used. Each control is preferably a duplex comprising first and second single stranded polynucleotides each preferably able to form a duplex with a single strand of the sample polynucleotide and or amplicons derived from the sample polynucleotide. For example, where the sample polynucleotide and or amplicons comprise two complementary polynucleotide strands, the control polynucleotide may comprise a first polynucleotide strand able to form a duplex with a first strand of the sample polynucleotide or amplicon and a second polynucleotide strand able to form a duplex with the complementary strand of the sample polynucleotide or amplicon.

Preferably, the sample polynucleotide is subjected to TGE in the presence of one of the controls along a first separation lane (upper half of FIG. 6). Along a second separation lane, or along the first separation lane at a preferably different time, the sample polynucleotide is subjected to TGE in the presence of a different control, which may be of the same type or different as the first control (lower half of FIG. 6). As shown schematically in FIG. 6, the electrophoresis data obtained from the TGE depends upon the control used and the genotype of the sample polynucleotide being tested. FIG. 7 shows electrophoresis data obtained upon subjecting a sample polynucleotide to TGE in the presence of a CC control polynucleotide following duplex formation. FIG. 8 shows electrophoresis data obtained upon subjecting a polynucleotide to TGE in the presence of a TT control polynucleotide following duplex formation. Second scores and final scores obtained from the electrophoresis data FIGS. 7 and 8 are also shown in FIG. 8. In either strategy, multiplexed samples with different lengths of DNA amplicons can be separated in along a single separation lane to achieve maximum efficiency of the technique (FIGS. 9, 10, 11, 12, and 13).

Figure 14:
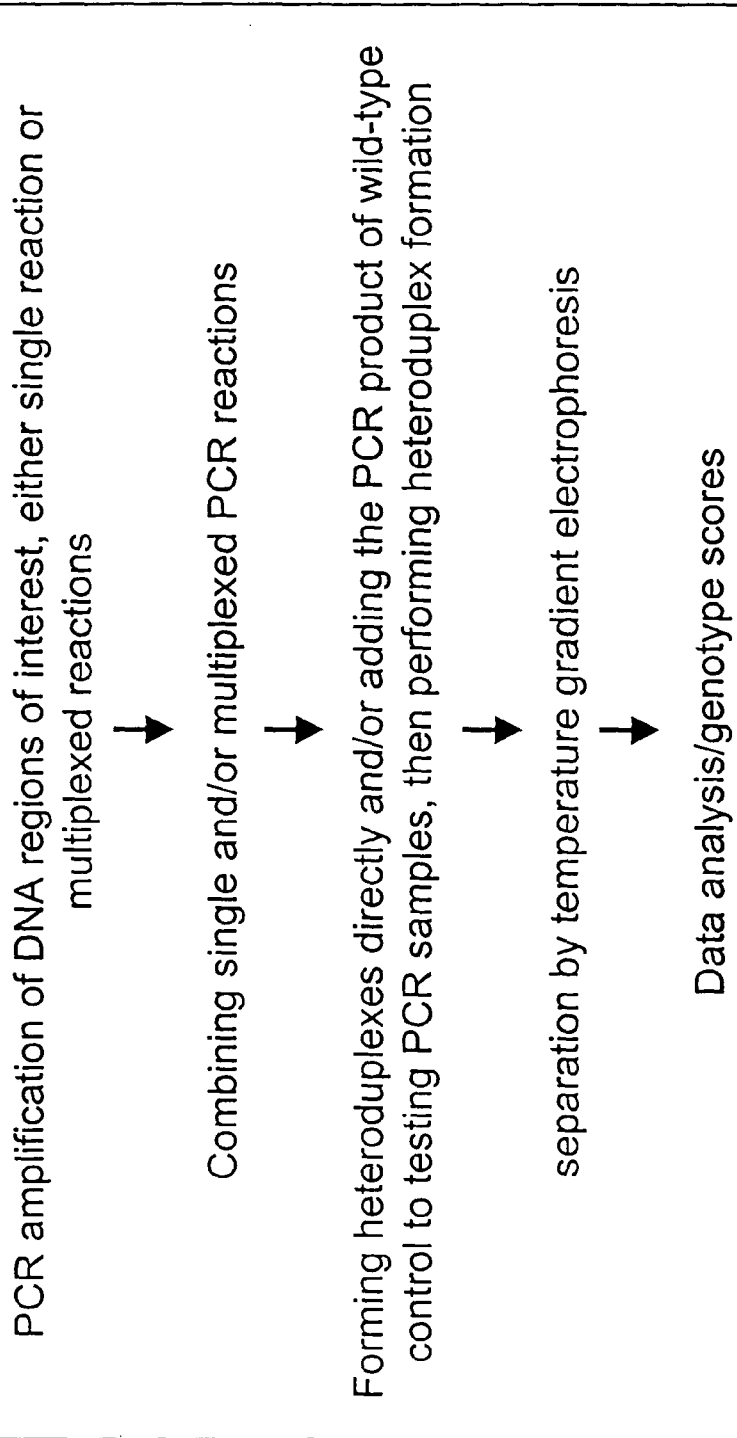
FIG. 14 shows a flowchart of a method of the invention.

Referring to the flow chart of FIG. 14, in one embodiment, the method of the invention comprises amplification, such as by polymerase chain reaction (PCR), of regions of interest of a polynucleotide containing a mutation or a SNP to prepare amplicons (FIG. 14). In any embodiment of the invention, the polynucleotide may be DNA, such as genomic DNA of an organism. The organism may be, for example, an animal (including mammals) or a plant. In a preferred embodiment, the polynucleotide is of a human.

The amplification may be performed by one or more amplification reactions, each of which amplifies a single polynucleotide region of interest or by a multiplexed reaction, which concomitantly amplifies a plurality of preferably different regions of interest. Different amplified regions of the polynucleotide may overlap, i.e., may include common regions of the polynucleotide. In any event, the amplification reaction provides amplicons, which may be PCR products. Amplicons of the may be, for example, wild-type homozygote, mutation homozygote, mutation heterozygote, or combinations thereof.

Amplicons prepared in accordance of the invention may be of different sizes. For example, the amplicons may have sizes of about 20 base pairs to about 1000 or even more base pairs. Amplicons of different sizes may have sequences that correspond to different regions of the polynucleotide. Alternatively, or in combination, amplicons of different sizes may be prepared from different polynucleotides. A plurality of the amplicons may be combined or pooled. For example, 5, 15, 20 or more amplicons can be pooled from individual and/or multiplex PCR reactions without any further post-PCR purification. As a consideration, a multiplexed PCR reaction or samples to be pooled and separated in a single channel with TGE preferably contain unrelated DNA sequences to prevent cross pairing of DNA strands from different amplicons. One or more duplexes, such as heteroduplexes and/or homoduplexes, may be prepared from the amplicons with or without pooling of amplicons of different sizes. For example, duplexes may be prepared by subjecting one or more amplicons to a denaturing and annealing step. Suitable methods for preparation of duplexes are disclosed in Applicant's copending U.S. application Ser. No. 10/287,826, filed Nov. 5, 2002, and incorporated herein.

The duplexes are subjected to a temperature gradient separation, such as (TGE), along one or more separation lanes. The separation lanes may be, for example, electrophoresis lanes such as capillaries, slab gels, or microfluidic structures. During electrophoresis, the migrating duplexes are subjected to a temperature ramp spanning melting temperatures (Tm's) for the homoduplexes and heteroduplexes. Heteroduplexes generally have lower Tm's than their corresponding homoduplexes due to the presence of a mismatch. Thus, heteroduplexes denature at a lower temperature than homoduplexes and will exhibit a retarded mobility in the gel, resulting in separation of heteroduplex and homoduplex species having the same lengths. Suitable temperature gradient electrophoresis methods and systems are disclosed in the copending 10/287,826 application.

Electrophoresis data indicative of the presence of the migrating heteroduplexes and homoduplexes is obtained, such as by using a laser-induced fluorescence detection system. The electrophoresis data may be used to distinguish amplicons indicative of the presence of (i) a mutation and or SNP from (ii) wild type.

One embodiment of the present invention relates to a computer readable medium comprising code. The code may prepare data, such as a visual display or printout, identifying the presence of DNA variants and preferably their genotypes. The data may be prepared automatically using electrophoresis data obtained from a TGE separation. Preferably, the computer readable medium comprises code to call a genotype for a test sample with each addition of two controls, and then combined two calls to generate a final call for a genotype of the testing sample; 2) defining a migration zone for a specific PCR product for a multiplexed-sample separation by TGE using a molecular ladder and/or a DNA control panel as a size calibration. The control panel can be assembled based on multiplexed samples, which are electrophoresed in a separate channel.

Sample Preparation.

To take full advantage of the separation capability of any instrumental platform (such as an automated capillary sequencing instrument), primer pairs for amplifying different DNA regions can be such designed that PCR products ranging from 100 to 800 bp will be generated. To ensure a clear separation of different lengths of DNA fragments, each PCR amplicon should be generated with 30-50 bp apart. Each PCR product can be a wild-type homozygote, a mutation homozygote or a mutation heterozygote. The PCR reaction can be performed with a single pair of primers for a single amplicon or multiple pairs of primers for multiple amplicons. The latter strategy would further reduce the time, labor and the cost of reagents for the assay. Multiplex PCR reactions, as disclosed in Elnifro et al. 2000, are known to those in the art.

Figure 10:
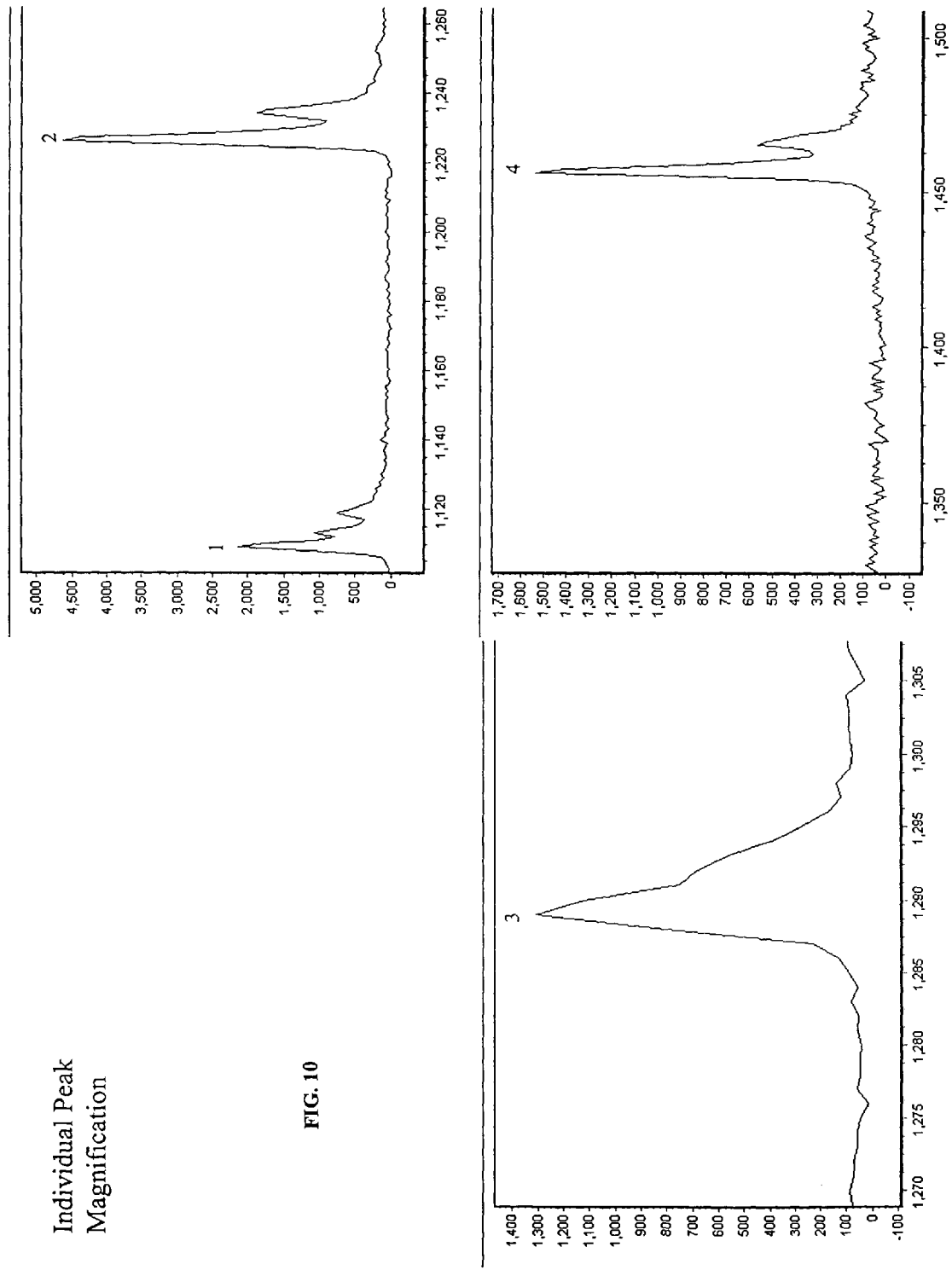
FIG. 10 shows detail of first four electrophoresis peaks of FIG. 9.
Figure 11:
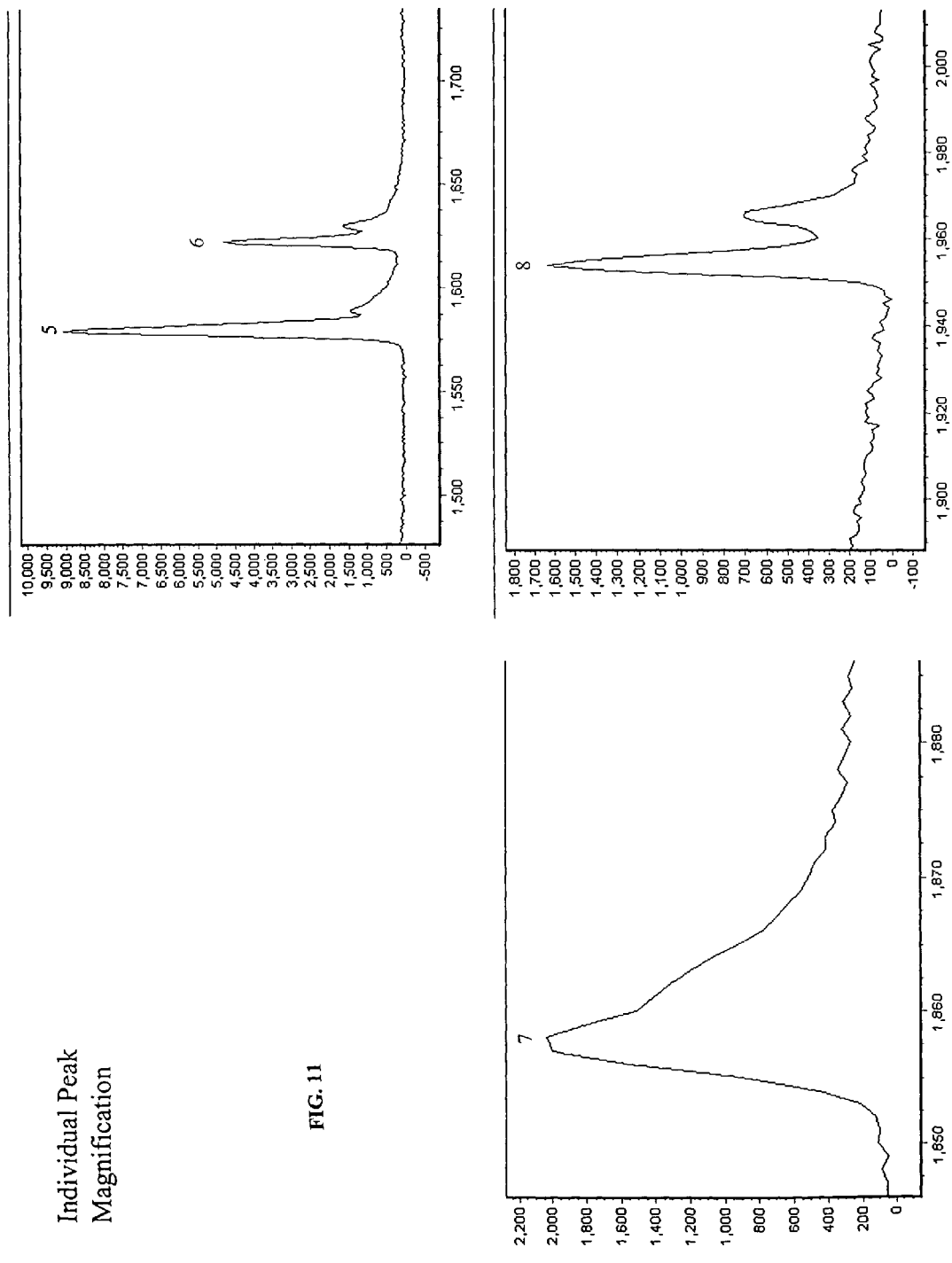
FIG. 11 shows detail of last four electrophoresis peaks of FIG. 9.
Figure 12:
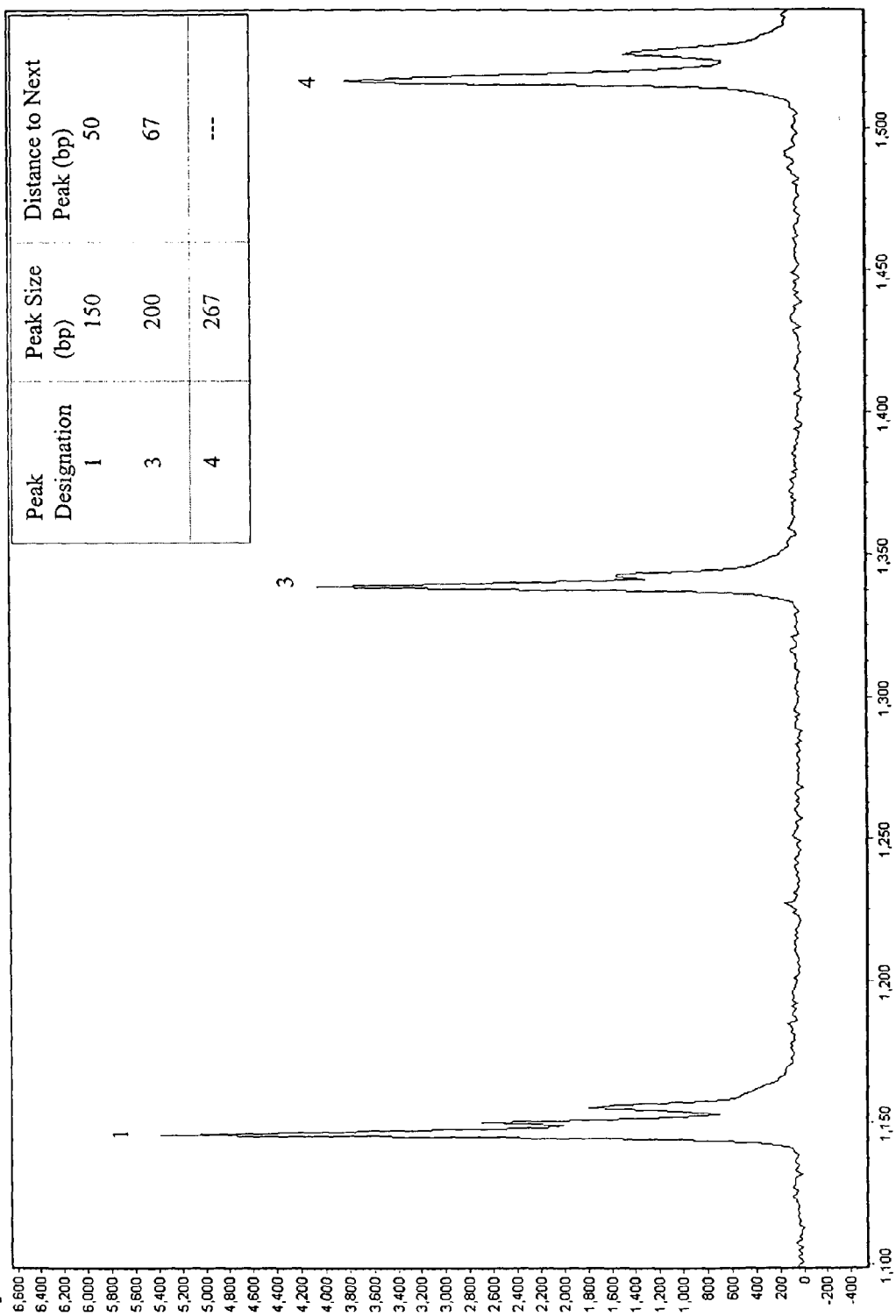
FIG. 12 shows electrophoresis data obtained from a multiplexed separation of three heterozygous samples along a single separation lane, X-axis: Frame number (migration time), Y-axis: signal intensity, peak numbers, corresponding DNA sizes and size difference in base pairs to next peak, PEO sieving matrix.
Figure 13:
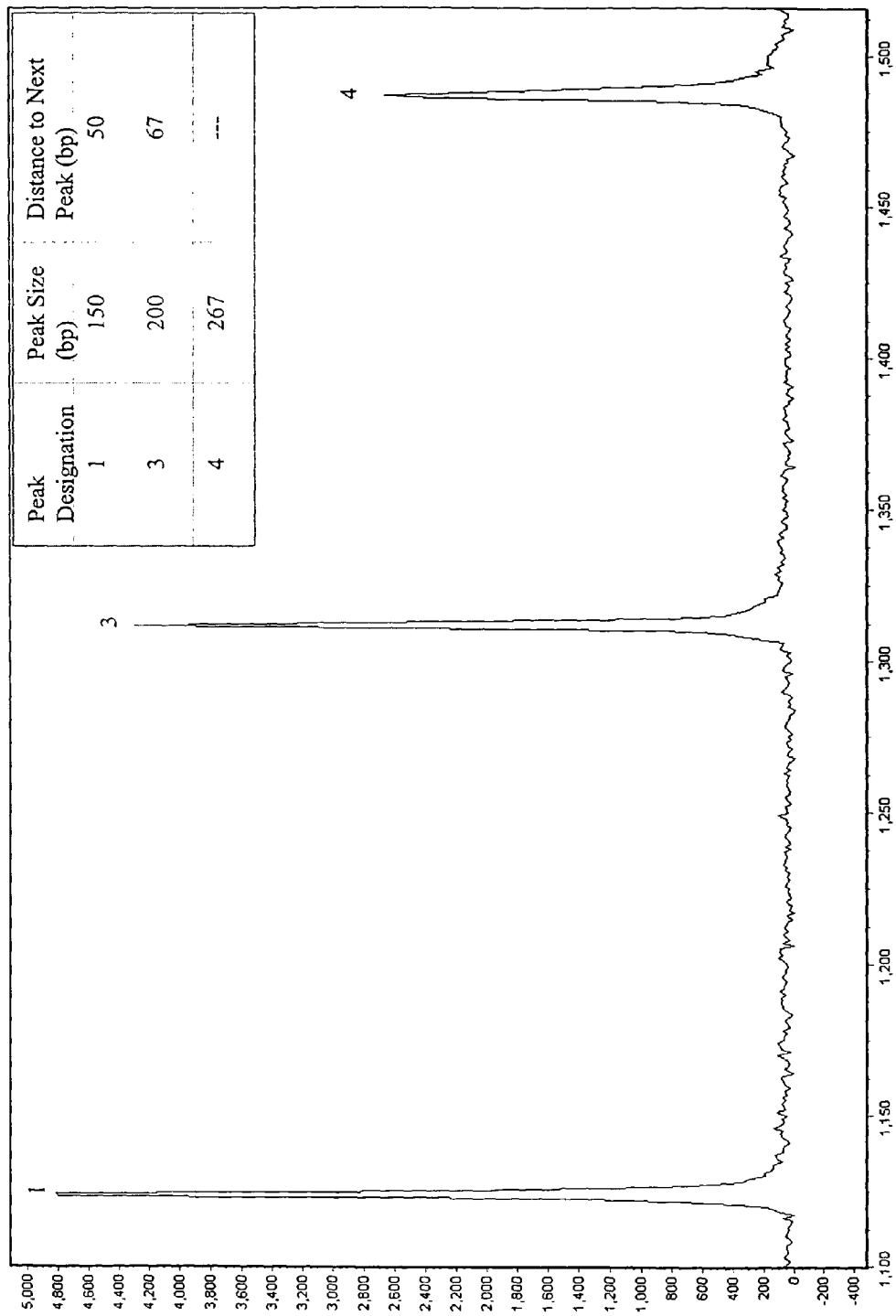
FIG. 13 shows electrophoresis data obtained from a multiplexed separation of three homozygous controls, corresponding to the three heterozygous samples of FIG. 12, X-axis: Frame number (migration time), Y-axis: signal intensity, peak numbers, corresponding DNA sizes and size difference in base pairs to next peak, PEO sieving matrix.

Multiplexing efficiency depends on how many base pairs separate the lengths of neighboring DNA fragments. The fewer the base pairs, the greater the multiplexing efficiency. FIG. 10 shows temperature electrophoresis data obtained for polynucleotides differing in size by from 20 to 119 base pairs. Therefore, one can easily multiplex 20 samples in a lane that can separated DNA fragments up to 800 bp. Moreover, the electrophoresis data of FIG. 9 demonstrate that a single temperature ramp, in this case 8° C., may be used to separate a plurality of samples present in a mixture. Therefore, the invention will provide not only a high-throughput method, but also a cost-efficient means to conduct DNA genotyping. For example, approximately 1,000 samples may be analyzed in two hours in a single run using a 96-capillary electrophoresis device, if 20 samples/capillary are included, with a cost of 1-2 cents. An example of a suitable electrophoresis device is disclosed in U.S. patent application Ser. No. 10/287,826, filed Nov. 5, 2002, which is incorporated herein in its entirety.

Addition of homozygous controls to the testing samples and multiplexed analysis.

Control DNA amplicons can be prepared in large quantity and add to the testing samples. The amplification efficiency for an amplicon with a same pair of primers targeting a same region of DNA is usually similar. Thus, a 1:1 mixture of the control and testing samples is usually sufficient for any amplicons. Even if there are small differences on concentrations of some amplicons between the control and the sample, it will not affect the final call since the peak pattern will still be very similar. We have resolved samples with 1:40 difference in concentration.

TGE Separation.

The homo- and heteroduplexes formed through denaturing and annealing process are then separated by the TGE method and detected by the LIF system. Using the TGCE system developed by SpectruMedix Corporation, the temperature gradient is provided by bathing capillary array in hot air that is circulated through a heater that is externally controlled by the instrument control computer. For TGCE analysis, crude samples can be directly injected into capillaries. The polyethylene oxide (PEO) gel matrix is used for electrophoresis. Optimization of the temperature profile for each sample is not required since the selected temperature ramp will cover Tms for all samples tested in the run. The temperature controller performs a predetermined temperature ramp, typically at a rate of 0.4 C/min. Under these conditions, the heteroduplex reaches the Tm earlier than its corresponding homoduplex due to the mismatch and thus exhibit a retarded mobility in the gel, resulting in separation from the homoduplex. Fluorescence from an intercalating dye is excited with an air-cooled argon ion laser at all line emission mode. A CCD camera was used to detect fluorescence from all 96 capillaries simultaneously. SpectruMedix CheckMate® software may be used for instrument control and data acquisition.

Automated software to report genotypes of DNA variants.

A computer program is created to report genotypes of DNA variants automatically after the TGE separation. There are two key features of the software: 1) calling a genotype for a test sample with each addition of two controls, and then combined two calls to generate a final call for a genotype of the testing sample; 2) defining a migration zone for a specific PCR product for a multiplexed-sample separation by TGE using a molecular ladder and/or a DNA control panel as a size calibration. The control panel can be assembled based on multiplexed samples, which are electrophoresed in a separate channel.

Figure 15:
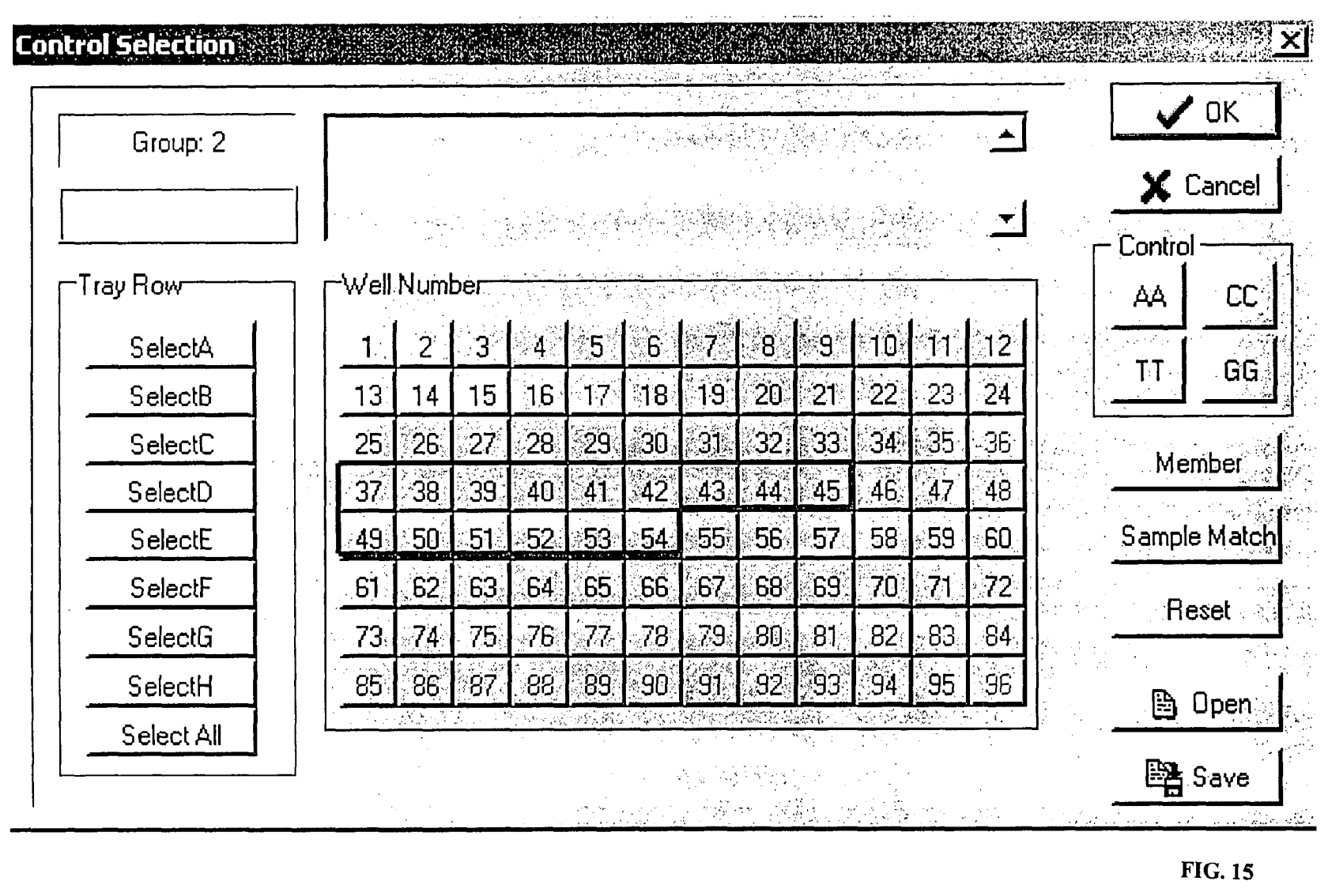

In practice, one may divide a 24-, 48-, 96-, or 384-well tray into two halves. One half runs original testing DNA samples, the other half runs the same set of testing samples mixed with one of the controls. Alternatively, one half runs the testing samples mixed with one control and the other half runs the same set of testing samples mixed with the other control. FIG. 15 shows a program interface on how the controls and a pair of the same set of sample can be selected and compared. The middle panel is the layout of a 96-well tray on which six such samples were run to prove the principle of concept. Samples 1-6 were mixed with the control CC and added to the wells 37-42. Whereas wells 49-54 were used to hold the same set of samples mixed with the other control TT. Wells 43, 44 and 45 contained CC, CT and TT controls.

Figure 17:
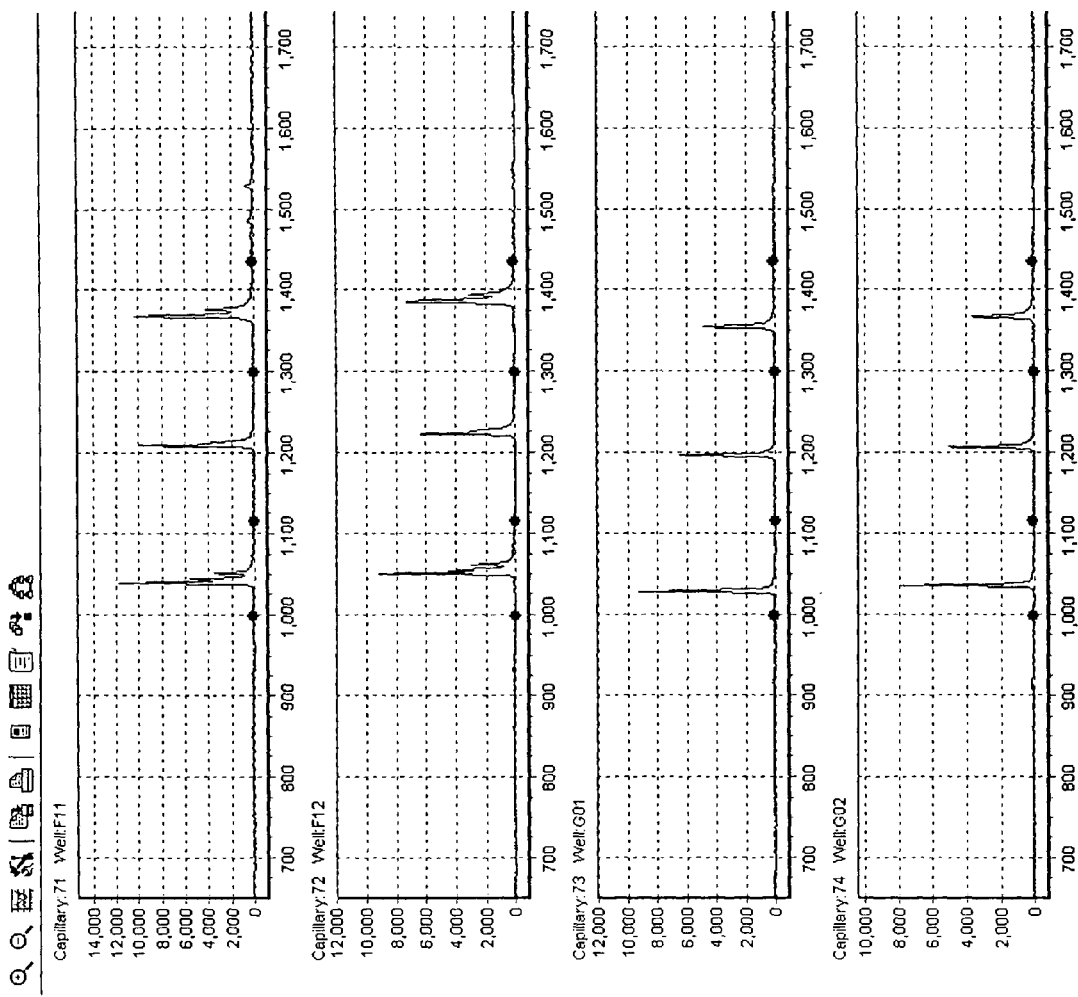
FIG. 17 illustrates use of a panel of controls and/or molecular ladders to define a migration zone for any specific sample.

One may select CC or TT polynucleotides (or combination thereof) as the control for samples in wells 37-42 or wells 49-54 to compare the peak patterns to see if any DNA variant is present. One then matches the wells of same sample for the down stream report. The up-panel of FIG. 16 shows the individual calls for samples mixed with either of the controls. The lower-panel indicates the final genotype scores for each sample. FIG. 17 shows an example of using a panel of controls as molecular ladders to define a migration zone for a specific PCR product in a multiplexed-sample separation by TGE.

Figure 18:
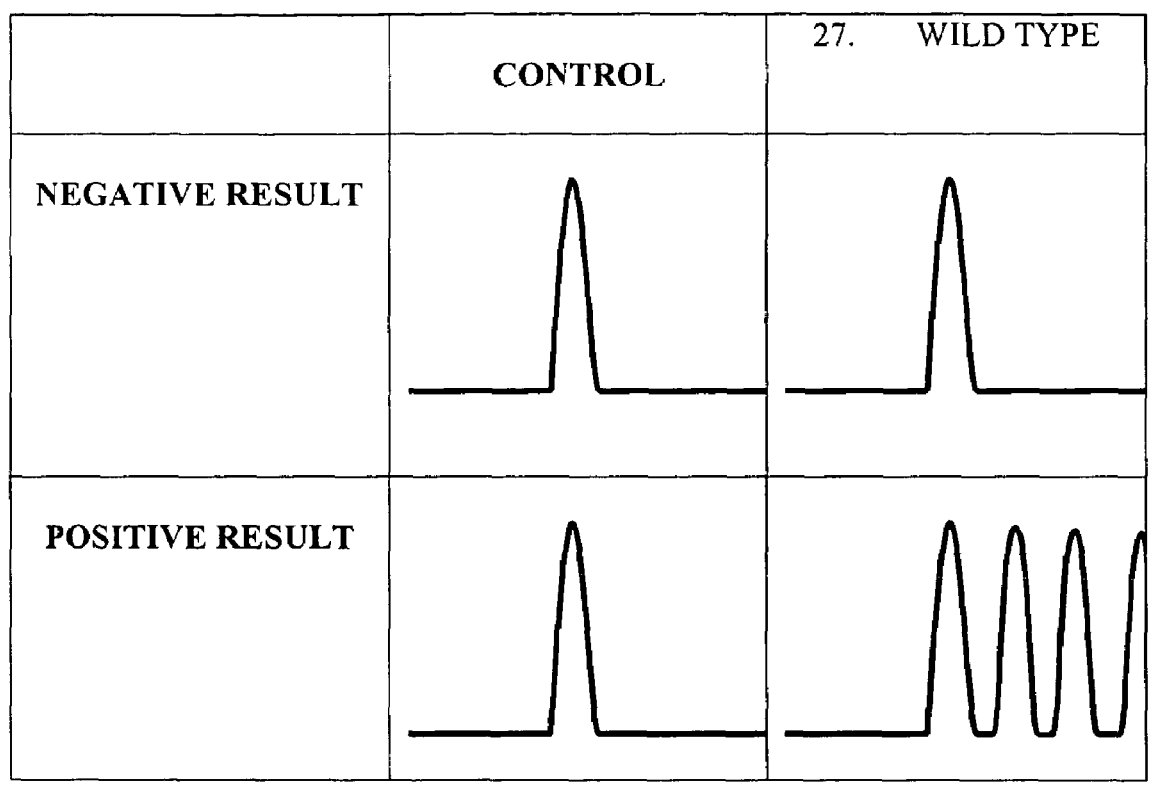
FIG. 18 illustrates a decision table for using electrophoresis data to determine whether a portion of a polynucleotide comprises a variant site, such as a polymorphism.

As shown in FIG. 18, one method of the invention comprises use of TGCE as a screening process. The data indicate the presence or absence of a polymorphism. Once a polymorphism is identified, "positive hits" are screened by conventional means. The benefit with a TGCE screening process is the reduction of the need to sequence large areas where there are no polymorphisms. In accordance with the method, a homoduplex standard may be subjected to TGCE in a separate lane. A determination of the variant state of the polynucleotide is based on comparing the unknown migration profile with the standard. A preferred embodiment of the current process employs an intercalating fluorescent dye (e.g., ethidium bromide). This reduces the cost of the analysis and simplifies the sample preparation. In this embodiment the analysis may employ single color detection.

As compared to known approaches, the present invention increases the amount of information obtained. The specific identity of the polymorphism may also be determined. Another distinction between the current approach and the present invention is the absence of a requirement that any homoduplex standard be run in another separation lane. The data obtained from running a matrix, such as a 2×3, of possibilities eliminates the need for running pure samples. Another distinction is that multiple duplex pairs differing in size may be combined and simultaneously subjected to TGE. This provides the ability to multiplex the number of mutation samples per electrophoretic lane. The end result of such multiplexing is a panel of duplexes, separated in time in the electrophoresis due to differing fragment size.

One embodiment of the present invention relates to a method for determining the identity of first and second bases of a DNA compound. First and second DNA control compounds are prepared. The first and second control DNA compounds differ by at least one base therealong. For example, one control compound may be CC and the other compound may be TT with respect to a particular site within the control compound. The first and second control DNA compounds may be duplexes.

The DNA compound may be combined with the first and second control DNA to form first and second mixtures. The mixtures may be subjected to at least one heating and cooling cycle to form heteroduplexes. The first and second mixtures are subjected to temperature gradient electrophoresis. The identity of the first and second bases of the DNA compound (i.e. the genotype of the DNA compound) is determined based on peaks obtained in the temperature gradient electrophoresis.

Figure 19:
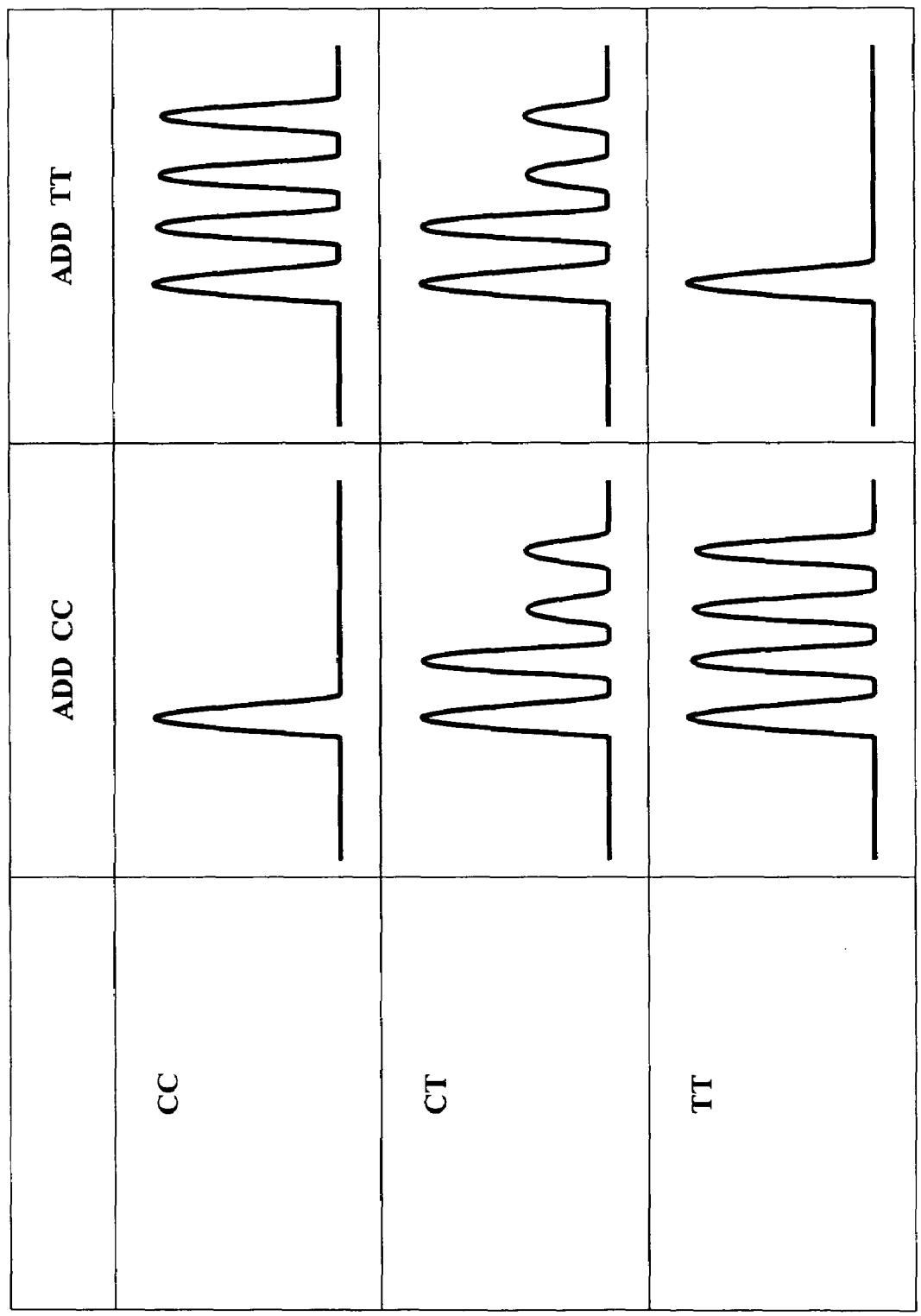
FIG. 19 illustrates a decision table for determining the genotype of a variant site of a sample polynucleotide based on first and second electrophoresis data.

Referring to FIG. 19, for example, the row designated CC shows the peak pattern expected if the DNA compound is of the CC genotype. Temperature gradient electrophoresis (TGE) in the presence of the CC control compound produces a single or narrow peak while TGE in the presence of the TT control compound produces a plurality of peaks or a single wider peak. In general, the CC genotype is determined if TGE produces a wider peak or plurality of peaks in the presence of the TT control compound than in the presence of the CC control compound. Similarly, referring to row 3, the presence of the TT genotype is determined if TGE produces a wider peak or plurality of peaks in the presence of the CC control compound than in the presence of the TT control compound. Referring to row 2 of FIG. 19, the CT genotype is determined if both TGE channels produce a plurality of peaks or a wider peak than expected for a single compound.

Peaks can be compared on the basis of, for example, peak width, such as full width half maximum, and peak area. The number of peaks can be determined by, for example, a derivative filter, such as a Savitzky Golay filter. The peaks obtained in a given TGE run can be compared to peaks in a look-up table to determine whether one or more peaks are present.

FIG. 19 may be summarized according to the following Boolean table:
If [1 peak] is observed with CC, and [plurality or wider peaks with TT; then sample polynucleotide=CC
If [plurality of peaks] with CC, and [plurality of peaks] with TT; then sample polynucleotide=CT
If [plurality of peaks or wider] with CC, and [1 peak] with TT; then sample polynucleotide=TT.

Referring to FIGS. 18 and 19, the method may be multiplexed to allow more than one mixture to be simultaneously subjected to TGE within a single separation lane. Each sample has a different migration time. Samples, having different sizes, are pooled together and subjected to TGE. Peaks within a given migration time range are analyzed to determine the presence of single or multiple peaks, as discussed above.

Referring to FIGS. 20 and 21, any method of the invention may be multiplexed to allow more than one mixture to be simultaneously subjected to TGE within a single separation lane. Each sample preferably a different migration time. Samples, having different sizes, are pooled together and subjected to TGE. Electrophoresis data is obtained. The data is indicative of the genotype of the sample polynucleotide or sample polynucleotides. Peaks within a given migration time range may be analyzed to determine the presence of single or multiple peaks, as discussed above.

The following references are incorporated to the extent necessary to understand the present invention:
A supplement to BioTechniques, SNPs: Discovery of markers for disease. June 2002.
Applied Biosystems, 2000, Protocol of ABI Prism SNaPshot Multiplex Kit.
Elnifro E., Ashshi A., Cooper R., and Klapper P. 2000. *Clinical Microbio. Rev.* 13:559-570.
Igloi G. 2001. *Genomics* 74:402-407.
Landergren U. M., Nilsson, and P-Y. Kwok. 1998. *Genome Res.* 8:767-776.
Ray R. and Norden B. 2000. *The FASEB J.* 14:1041-1060.
Ross P., Hall L., Smirnov I., and Haff, L. 1998. *Nature Biotechnol.* 16:1347-1351.
Wang D. G. et al., 1998. *Science.* 280:1077-1082.

What is claimed is:

1. A method of determining the genotype of a sample polynucleotide having at least a first variant site, comprising:
   amplifying at least a portion of the sample polynucleotide to obtain first amplicons, the first amplicons including the first variant site;
   combining the first amplicons with first and second different polynucleotide controls, the first and second polynucleotide controls differing by at least one base therealong, the position of the at least one differing base corresponding to the first variant site of the sample polynucleotide;
   preparing a plurality of first duplexes, each of at least some of the first duplexes comprising (i) a polynucleotide strand of one of the first amplicons and (ii) a complementary polynucleotide strand of the first polynucleotide control;
   preparing a plurality of second duplexes, each of at least some of the second duplexes comprising (i) a polynucleotide strand of one of the first amplicons and (ii) a complementary polynucleotide strand of the second polynucleotide control;
   subjecting the first and second duplexes to temperature gradient electrophoresis (TGE) to obtain first and second electrophoresis data; and
   determining the genotype of the first variant site of the sample polynucleotide based on the first and second electrophoresis data.

2. The method of claim 1, wherein determining the genotype of the sample polynucleotide comprises determining a number of peaks present in the first electrophoresis data and a number of peaks present in the second electrophoresis data.

3. The method of claim 1, wherein the first duplexes and second duplexes are subjected to TGE along first and second different separation lanes.

4. The method of claim 1, wherein the first and second polynucleotide controls are wild-type polynucleotides.

5. The method of claim 1, comprising:
   amplifying at least a second different portion of the sample polynucleotide to obtain second amplicons, the second amplicons including a second variant site of the sample polynucleotide;
   combining the second amplicons with third and fourth different polynucleotide controls, the third and fourth polynucleotide controls differing by at least one base therealong, the position of the at least one differing base corresponding to the second variant site of the sample polynucleotide;
   preparing a plurality of third duplexes, each of at least some of the third duplexes comprising (i) a polynucleotide strand of one of the second amplicons and (ii) a complementary polynucleotide strand of the third polynucleotide control;
   preparing a plurality of fourth duplexes, each of at least some of the fourth duplexes comprising (i) a polynucleotide strand of one of the second amplicons and (ii) a complementary polynucleotide strand of the fourth polynucleotide control;
   subjecting the third and fourth duplexes to temperature gradient electrophoresis (TGE) to obtain third and fourth electrophoresis data; and determining the genotype of the second variant site of the sample polynucleotide based on the third and fourth electrophoresis data.

6. The method of claim 5, wherein at least one of the first and second duplexes has a size that differs from at least one of the third and fourth duplexes and wherein subjecting the first and second duplexes to TGE and subjecting the third and fourth duplexes to TGE comprise simultaneously subjecting at least 3 duplexes of the first, second, third, and fourth duplexes to TGE along the same separation lane.

7. The method of claim 6, wherein at least one of the first and second duplexes has a size that differs from at least one of the third and fourth duplexes by at least 20 base pairs.

8. The method of claim 1, comprising:
amplifying at least a first portion of a second different sample polynucleotide to obtain second amplicons, the second sample polynucleotide comprising a second variant site, the second amplicons including the second variant site of the sample polynucleotide;
combining the second amplicons with third and fourth different polynucleotide controls, the third and fourth polynucleotide controls differing by at least one base therealong, the position of the at least one differing base corresponding to the second variant site of the second sample polynucleotide;
preparing a plurality of third duplexes, each of at least some of the third duplexes comprising (i) a polynucleotide strand of one of the second amplicons and (ii) a complementary polynucleotide strand of the third polynucleotide control;
preparing a plurality of fourth duplexes, each of at least some of the fourth duplexes comprising (i) a polynucleotide strand of one of the second amplicons and (ii) a complementary polynucleotide strand of the fourth polynucleotide control
subjecting the third and fourth duplexes to temperature gradient electrophoresis (TGE) to obtain third and fourth electrophoresis data; and
determining the genotype of the second variant site of the sample polynucleotide based on the third and fourth electrophoresis data.

9. The method of claim 8, wherein at least one of the first and second duplexes has a size that differs from at least one of the third and fourth duplexes and wherein subjecting the first and second duplexes to TGE and subjecting the third and fourth duplexes to TGE comprise simultaneously subjecting at least 3 duplexes of the first, second, third, and fourth duplexes to TGE along the same separation lane.

10. The method of claim 9, wherein at least one of the first and second duplexes has a size that differs from at least one of the third and fourth duplexes by at least 20 base pairs.

11. A method for determining the genotype of a sample polynucleotide, compnsing:
providing first and second polynucleotide controls, the first and second polynucleotide controls differing by at least one base therealong, the position of the differing base corresponding to a position of a variant site of the sample polynucleotide;
combining a first amount of the sample polynucleotide with the first polynucleotide control to prepare a first mixture, each of the sample polynucleotide and the first polynucleotide control comprising a polynucleotide strand sufficiently complementary to form a duplex with a polynucleotide strand of the other of the sample polynucleotide and first polynucleotide control;
forming first duplexes, at least some of the first duplexes comprising a strand of the sample polynucleotide and a strand of the first polynucleotide control;
combining a first amount of the sample polynucleotide with the second polynucleotide control to prepare a second mixture, each of the sample polynucleotide and the second polynucleotide control comprising a polynucleotide strand sufficiently complementary to form a duplex with a polynucleotide strand of the other of the sample polynucleotide and second polynucleotide control;
subjecting the first and second mixtures to temperature gradient electrophoresis to obtain first and second electrophoresis data;
and determining the genotype of the sample polynucleotide based on the first and second electrophoresis data.

12. The method of claim 11, wherein determining the genotype of the sample polynucleotide comprises determining a number of peaks present in the first electrophoresis data and a number of peaks present in the second electrophoresis data.

13. The method of claim 11, wherein both the first and second polynucleotide controls are homozygous.

14. The method of claim 11, wherein the sample polynucleotide comprises an amplicon prepared by amplifying a first double stranded polynucleotide.

* * * * *